(12) United States Patent
Kennedy et al.

(10) Patent No.: US 12,091,489 B1
(45) Date of Patent: Sep. 17, 2024

(54) MULTIPLY-CROSSLINKED POLYISOBUTYLENE-BASED POLYURETHANES AND THEIR PREPARATIONS AND USES THEREOF

(71) Applicants: Joseph P. Kennedy, Akron, OH (US); Turgut Nugay, Sariyer-Istanbul (TR)

(72) Inventors: Joseph P. Kennedy, Akron, OH (US); Turgut Nugay, Sariyer-Istanbul (TR)

( * ) Notice: Subject to any disclaimer, the term of this patent is extended or adjusted under 35 U.S.C. 154(b) by 0 days.

(21) Appl. No.: 18/602,926

(22) Filed: Mar. 12, 2024

Related U.S. Application Data

(60) Provisional application No. 63/536,421, filed on Sep. 3, 2023, provisional application No. 63/471,189, filed on Jun. 5, 2023.

(51) Int. Cl.
| | | |
|---|---|---|
| *C08G 18/62* | (2006.01) | |
| *A61F 2/24* | (2006.01) | |
| *C08G 18/12* | (2006.01) | |
| *C08G 18/24* | (2006.01) | |
| *C08G 18/32* | (2006.01) | |
| *C08L 75/04* | (2006.01) | |

(52) U.S. Cl.
CPC ............ *C08G 18/6204* (2013.01); *A61F 2/24* (2013.01); *C08G 18/12* (2013.01); *C08G 18/242* (2013.01); *C08G 18/3206* (2013.01); *C08G 18/3228* (2013.01); *C08L 75/04* (2013.01); *C08L 2312/00* (2013.01)

(58) Field of Classification Search
None
See application file for complete search history.

(56) References Cited

U.S. PATENT DOCUMENTS

| | | | | |
|---|---|---|---|---|
| 5,428,123 A | * | 6/1995 | Ward ................. | C08G 18/4808 |
| | | | | 210/500.21 |
| 9,926,399 B2 | * | 3/2018 | Faust ................. | C08G 18/6511 |
| 10,618,999 B2 | * | 4/2020 | Kennedy ............ | C08G 18/6204 |
| (Continued) | | | | |

OTHER PUBLICATIONS

Akoet al., âPolyisobutylene-based urethane foams I. Comparative reactivities of hydroxyl-terminated polyisobutylene-diols and—triols and other hydroxyl-capped polyols with isocyanateâ, Polymer Bulletin 19(2), 137-143 (1988) (Year: 1988).*

*Primary Examiner* — Michael M Dollinger
(74) *Attorney, Agent, or Firm* — Renner, Kenner, Greive, Bobak, Taylor & Weber

(57) ABSTRACT

A multiply-crosslinked polyisobutylene-based polyurethane includes a plurality of multi-telechelic polyisobutylene-based segments and a plurality of urethane segments having a plurality of chain extender-based segments therein. Each end of one of the plurality of urethane segments is linked either to an end of one of the plurality of multi-telechelic polyisobutylene-based segments, or to an end of one of the plurality of chain extender-based segments. Also, one or more of the plurality of urethane segments are physically crosslinked to one or more other of the plurality of urethane segments. Notably, the plurality of multi-telechelic polyisobutylene-based segments constitute at least 70 weight percent of the polyisobutylene-based polyurethane and the plurality of urethane segments, including the plurality of chain extender-based segments therein, constitute up to 30 weight percent of the polyisobutylene-based polyurethane.

23 Claims, 8 Drawing Sheets

(56) References Cited

U.S. PATENT DOCUMENTS

2016/0122464 A1* 5/2016 Seppala .............. C08G 18/73
  528/76
2019/0127510 A1* 5/2019 Kennedy .............. C07C 23/32

* cited by examiner

MULTIPLY-CROSSLINKED POLYISOBUTYLENE-BASED POLYURETHANES AND THEIR PREPARATIONS AND USES THEREOF

CROSS-REFERENCE TO RELATED APPLICATIONS

This application claims the benefit of U.S. Provisional Patent Application No. 63/471,189 filed Jun. 5, 2023, and claims the benefit of U.S. Provisional Patent Application No. 63/563,421 filed Sep. 3, 2023, the disclosures of which are incorporated herein by reference.

FIELD OF THE INVENTION

The present invention relates to a new class of hybrid thermoplastic/thermoset elastomers. More particularly, the present invention relates to multiply-crosslinked polyisobutylene-based polyurethanes and their preparations and uses. The term "multiply-crosslinked" means that, in these polyisobutylene-based polyurethanes, both the diisocyanate/urethane-based segments or diisocyanate/urethane-urea-based segments, i.e., the "hard" domains, and polyisobutylene-based segments, i.e., the "soft" domains, are independently crosslinked using different methodologies. Specifically, the hard (diisocyanate-based) domains are crosslinked by physical (crystalline) forces via H-bonding, while the soft (polyisobutylene-based) domains are crosslinked by multi-functional alcohols, creating permanent chemical bonds. The preparation of such multiply-crosslinked polyisobutylene-based polyurethanes and their uses, particularly for indwelling medical devices such as heart valves and the like, are also noted.

BACKGROUND OF THE INVENTION

Polyisobutylene-based polyurethanes (PIB-PUs) are generally a well-known class of thermoplastic elastomers consisting of hard polyurethane (PU) or polyurethane-urea (PUU) domains and soft polyisobutylene-based (PIB) domains. Generally, PIB-PUs are formed by the reaction product of a polyisobutylene diol (also called a di-telechelic, hydroxy-terminated polyisobutylene) and a diisocyanate, such as methylene diphenyl diisocyanate (MDI), and a low-molecular weight diol chain-extender, such as 1,4-butanediol, to further react with the diisocyanate to form the PIB-PU. It is generally known that such PIB-PUs exhibit lesser mechanical properties than conventional polyurethanes (e.g., commercially-available polyether-, polyester-, polycarbonate-, and polysiloxane-based polyurethanes) mainly because there is insufficient stress transfer between the highly segregated polar hard and apolar soft domains, and, importantly, insufficient H bonding between different segments. However, PIB-PUs are generally considered to be far more biologically stable, since conventional polyurethanes are generally known to be vulnerable to hydrolytic and oxidative damage (mainly on account of the many —$CH_2$—O— linkages they contain in the soft segment). PIB-PUs are far more chemically resistant as their soft segments contains only highly stable —$CH_2$—$C(CH_3)_2$— units.

Generally, linear polyisobutylene-based polyurethane-ureas (PIB-PUUs) are produced in the same manner as PIB-PUs, wherein PIB-diols form the soft segment and a diisocyanate, such as methylene diphenyl diisocyanate (MDI), and a well-defined combination of two kinds of chain extenders (e.g., a low molecular weight diol as chain extender and a low molecular weight diamine or amino alcohol as co-chain extenders) form the hard segments). Thus, PIB-PUUs are typically stronger (exhibit higher tensile stresses) than polyurethanes because of the presence of stronger bifurcated H bonds in the former.

It should be understood that PIB-PUUs are not polyureas. To the extent that the PIB-PUUs are understood to include only diamine-based chain extenders, and are not polyureas (which should be understood to be the reaction product of a diamine with diisocyanate) themselves, they are, in fact, a subset of PIB-PUs. Thus, the use of the term polyisobutylene-based polyurethanes (or "PIB-PUs") will be used to describe both PIB-PUs and PIB-PUUs herein. However, PIB-PUUs and polyureas are fundamentally different. While PIB-based polyurethane-ureas are desirably melt processible, polyureas, on account of strong bifurcated H bonds, do not melt but degrade before melting. As a result, heretofore, polyureas can only be solution processed by using strongly H-accepting environmentally objectionable solvents, (i.e., dimethyl acetamide, dimethyl formamide). The creation of PIB-PUUs having enhanced mechanical properties, while maintaining the melt processability of PUs in general and thermoplastic elastomeric PUs in particular is the subject of U.S. Pat. No. 10,618,999, the disclosure of which is incorporated herein by reference.

The synthesis, properties and uses of PIB-PUs have been intensively investigated in recent years. Among the many potential applications of these materials, includes their use in long-term implantable (indwelling) medical devices, in particular, for fully synthetic heart valve prostheses. PIB-PU heart valves promise to be superior to currently used mechanical and tissue valves made of pig and/or cow cardiac tissues, or of various synthetic materials, e.g., siloxane-based devices. Both currently used mechanical and tissue valves are transformative of life quality, and potentially lifesaving, for their recipients; but both also have drawbacks.

Mechanical valves are made of hard materials, typically metals, often coated in pyrolytic carbon; modern ones have a tilting disc design, which is far from the natural anatomy. Mechanical valves are extremely reliable and will last a lifetime. Their disadvantage is that because of the non-physiological blood flow which results from their operation, it is necessary for patients to take lifelong anti-coagulant medication, normally drugs such as warfarin; with severe impacts on quality of life and potential bleeding complications. Warfarin is also incompatible with pregnancy.

Bioprosthetic valves are made from fixed animal tissue, normally pig aortic valves or bovine pericardium, stitched onto a metal or PEEK frame. Tissue valves behave very much like the natural valve and so result in physiological blood flow, negating the need for long term anti-coagulation medication. However, because the tissue is dead, it has a limited lifetime in the body, typically not more than 10-15 years. One commercial company recently discontinued selling its prosthesis due to deterioration after 10 years. Failure normally results from calcification of the fixed tissue and calcification is quicker in younger patients, so valve lifetime tends to be shorter in such individuals who actually need the valve for longer. These prostheses are individually handmade, inefficiently by cutting and sewing carefully selected bovine or porcine cardiac tissue. Tissue must be harvested from animals specially grown in hygienic facilities, and 99% is wasted. This results in significant supply chain and animal welfare concerns. Current clinical practice is to recommend mechanical valves for younger patients (with the exception of younger women wishing to have children), and tissue valves for those over approximately 65 years of age. It is also worth mentioning that tissue valves are very expensive ($1,000-4,000 each).

Thus, the need exists for heart valve prostheses and other indwelling devices that employ a material that has excellent mechanical properties, has a lifelong or nearly lifelong durability in patients, and has no requirement for long-term anticoagulation therapy.

In recent years, polymeric heart valves and indwelling devices have been produced. However, none of the polymeric heart valves have yet been set forth for human clinical testing. The reason for the lack of successful translation to clinical practice has primarily come down to the materials' limitation of the polymers developed to date. Accordingly, the need exists for new polymeric materials that can provide hard domains for excellent mechanical properties, as well as melt processability and flexibility as provided by soft domains of the material.

Furthermore, it is noted that the synthesis and characterization of Ø(PIB-OH)3, i.e., a 3-arm star PIB terminated with an —OH end group on each arm, has been long developed in the prior art. Such multi-arm star PIB polymers are produced by cationic polymerization of a initiator core from which three (and sometimes more, hence, the word "multi-arm") polyisobutylene arms are polymerized. The PIB arms are terminated so as to result in with a —OH group at the end of each arm.

Thus, the need exists for the production of PIB-PUs that have sufficient processability and better mechanical properties than other PIB-PUs already known in the art. Noting that polyureas can provide the better mechanical properties, but are insufficiently processable, one of ordinary skill in the art would think that simply finding an optimization of a mixture of diols and diamines would suffice. However, it does not. As unexpectedly found in this disclosure, more is necessary. Accordingly, new methodologies are necessary to provide highly biocompatible, biostable, longer lasting, stronger, softer, more elastic, compliant, and calcification resistant materials having higher durability and dynamic fatigue resistance.

SUMMARY OF THE INVENTION

While the synthesis and characterization of Ø(PIB-OH)3, i.e., the 3-arm star PIB terminated with —OH end groups, is known, it is unknown to use a multi-arm star PIB polymer as a crosslinking agent for the preparation of xPIB-PU (or xPIB-PUU, which is understood to be a subset of xPIB-PU). As used herein, the abbreviation of polyisobutylene-based polyurethane is PIB-PU, while the abbreviation of polyisobutylene-based polyurethane-urea is PIB-PUU. The letter x in front of PIB-PU, such as xPIB-PU, indicates crosslinked PIB-PU. Where there is a numeral subscript following the "x," or an "n" subscript, it will be understood as indicating the specific number of kinds of crosslinks, for example, $x_2$PIB-PU stands for a PIB-PU crosslinked by two kinds of crosslinking methods, for example, by H bonds (physical crosslinking) and by the reaction of the polyol, e.g., Ø(PIB-OH)3, with a diisocyanate (chemical crosslinking). It will be appreciated that one could consider PIB-PU to be a cross-linked PIB-PU, given that physical crosslinking of the hard PU domains does exist in the polyurethane. However, for purposes of this invention it will be understood that by the term "crosslinked PIB-PU" or xPIB-PU, we mean multiply-crosslinked, i.e., have more than one type of crosslinking. In other words an xPIB-PU is both physically and chemically crosslinked.

Moreover, this is believed to be the first use of a crosslinking agent for the preparation of xPIB-PU. While urethane bond formation between the prepolymer and Ø(PIB-OH)3 was expected (see the scheme in FIG. 1), the practical consequences caused by the number average molecular weights of the crosslinking agent on processability time were completely unexpected. Unexpectedly, it has been found that xPIB-PU must be produced with at least 70 wt. % PIB, and that the number average MW of this crosslinking agent (Ø(PIB-OH)3) must be in the 3,000-10,000 g/mole range. It has also unexpectedly been found that the processability period of xPIB-PU can be controlled by blends of the crosslinking agent with ditelechelic PIB-OH; for example, using blends of Ø(PIB-OH)3 and OH-ditelechelic PIBs, having well-defined number average MWs. To date, no other disclosure for the production of polyurethane has been prepared with blends of two well-defined number average MW PIBs, wherein one is a crosslinking agents (Ø(PIB-OH)3) and the other is a PIB diol.

One aspect of the present invention provides a multiply-crosslinked polyisobutylene-based polyurethane comprising a co-network of a plurality of multi-telechelic polyisobutylene-based segments and a plurality of urethane segments having a plurality of chain extender-based segments therein. Importantly, each end of one of the plurality of urethane segments is linked either to an end of one of the plurality of multi-telechelic polyisobutylene-based segments, or to an end of one of the plurality of chain extender-based segments. However, beyond that, there is a further crosslinking, wherein one or more of the plurality of urethane segments are physically crosslinked to one or more other of the plurality of urethane segments. It is noted that this crosslinking system cannot be produced unless the plurality of multi-telechelic polyisobutylene-based segments constitute at least 70 to 99 weight percent of the polyisobutylene-based polyurethane and the plurality of urethane segments, including the plurality of chain extender-based segments therein, constitute from 1 up to 30 weight percent of the polyisobutylene-based polyurethane. That, is both the polyisobutylene-based segments, noted and defined herein as the soft domain, and the urethane segments, including the chain extender-based segments therein, noted and defined herein as the hard domain, must be present. In other embodiments, the system used includes the plurality of multi-telechelic polyisobutylene-based segments constituting at least 70 to 90 weight percent of the polyisobutylene-based polyurethane and the plurality of urethane segments, including the plurality of chain extender-based segments therein, constituting from 10 up to 30 weight percent of the polyisobutylene-based polyurethane. In still other embodiments, the system used includes the plurality of multi-telechelic polyisobutylene-based segments constituting at least 70 to 85 weight percent of the polyisobutylene-based polyurethane and the plurality of urethane segments, including the plurality of chain extender-based segments therein, constituting from 15 up to 30 weight percent of the polyisobutylene-based polyurethane.

As used herein, the term "polyisobutylene-based segments" is defined as the resultant polyisobutylene reaction product left within the polyurethane as a result of the reaction of the polyisobutylene with hydroxy (—OH) terminal groups (or amine (—$NH_2$) terminal groups with diisocyanate. This may also be defined as the "soft domain," inasmuch as polyisobutylene is much softer, has lower mechanical properties, and is more flexible than the diisocyanate to which it is reacted. Thus, in at least one embodiment, the plurality of multi-telechelic polyisobutylene-based segments are the polyisobutylene segments resulting from the reactions of a plurality of polyisobutylene polyols with diisocyanate. In other embodiments, the plurality of multi-telechelic polyisobutylene-based segments are the polyisobutylene segments resulting from the reactions of a blend of a plurality of polyisobutylene polyols and a plurality of polyisobutylene polyamines with diisocyanate.

Likewise, the "plurality of urethane segments" are defined as the resultant diisocyanate reaction product left within the polyurethane as a result of the reaction of the polyisobutylene with hydroxy (—OH) or amine (—NH$_2$) terminal groups with diisocyanate. Each segment essentially forms a urethane group. This may also be defined as the "hard domain," inasmuch as it is harder, has better mechanical properties, and is less flexible that the polyisobutylene to which it is reacted.

The term "chain extender-based segments" is defined as the resultant short chain (C2 to C8) polyols or polyamines reaction products left within the polyurethane (or polyurethane-urea) that form larger lengths of urethane or urea groups as a result of the reaction of the short chain polyols/polyamines with diisocyanate, generally after the reactions between the polyisobutylene and diisocyanate has occurred. With a stoichiometric excess of diisocyanate, there will be ends of isocyanate that will reaction with the polyols or polyamines of the chain extender to crosslink the urethanes together. Thus, as the chain extenders are so short, they do not act like polyisobutylene, but rather are set forth within the hard domains as crosslinkers of urethane groups.

In at least one embodiment, the plurality of multi-telechelic polyisobutylene-based segments can be a plurality of tri-telechelic polyisobutylene triol-based (Ø(PIB-OH)3) segments. In at least another embodiment, the plurality of multi-telechelic polyisobutylene polyol segments can be a plurality of di-telechelic polyisobutylene diol-based (Ø(PIB-OH)2) segments. In yet another embodiment, the plurality of multi-telechelic polyisobutylene-based segments can be a blend or combination of both a plurality of tri-telechelic polyisobutylene triol-based (Ø(PIB-OH)$_3$) segments and a plurality of di-telechelic polyisobutylene diol-based (Ø(PIB-OH)$_2$) segments. Of course, it will also be appreciated that if a greater number of polyisobutylene arms are initiated as is known in the art, then the plurality of multi-telechelic polyisobutylene-based segments will have a plurality of telechelic polyisobutylene-based segments that match the number of arms produced in the preparation of the polyisobutylene star polymer having —OH (or —NH$_2$) terminal ends. It will also be appreciated that all of the plurality of polyisobutylene-based segments constitute the soft domains of the polyurethane. Still further, it should be understood that polyisobutylene star polymers having 3 or more arms are considered to be "crosslinked" chemically as the term is commonly defined. However, where a polyisobutylene is simply di-telechelic, having only two functional terminal end groups, it is not considered to be crosslinked, as the polymer will simply form a co-polymer chain.

In at least one embodiment, the plurality of chain extender-based segments can be a plurality of short chain (C2 to C8) polyol-based segments. In another embodiment, one or more chain extender-based segments can be a short chain (C2 to C8) polyamine-based segment, with one or more other chain extender-based segments being a short chain (C2 to C8) polyol-based segment. In at least one embodiment, the short chain (C2 to C8) polyol-based segments can be diol-based segments. It will be appreciated that these diol-based segments are simply chain extenders and not crosslinked. In other embodiments, the short chain (C2 to C8) polyol-based segments can be triol-based segments. It will be appreciated that these triol-based segments are crosslinked, and as such the triol-based chain extenders can be referred to as "crosslinking agents." In still other embodiments, the short chain polyol-based segments can be a blend or combination of both diol and triol segments. In yet other embodiments, the chain extender-based segments can be polyol-based and/or polyamine-based segments having two and/or three —OH or —NH$_2$ ends. Where the chain extender-based segment is obtained from a polyol or polyamine having three or more ends, the chain extender-based segment will be tri-telechelic or greater than tri-telechelic, respectively.

In at least one embodiment, a multiply-crosslinked polyisobutylene-based polyurethane as described above may have a plurality of multi-telechelic polyisobutylene-based segments that are a blend of a plurality of tri-telechelic polyisobutylene triol (Ø(PIB-OH)$_3$)-based segments, and a plurality of linear di-telechelic polyisobutylene diol (Ø(PIB-OH)$_2$)-based segments. In such an embodiment, each end of one of the plurality of urethane segments can be linked to one of (a) an end of one of the plurality of tri-telechelic polyisobutylene triol-based segments, (b) an end of one of the plurality of linear di-telechelic polyisobutylene diol-based segments, and (c) an end of one of said plurality of chain extender-based segments. Again, however, the plurality of tri-telechelic polyisobutylene triol-based segments and linear di-telechelic polyisobutylene diol-based segments should constitute at least 70 weight percent of the polyisobutylene-based polyurethane.

Notably, the polyiobutylene-based polyurethane is at least twice cross-linked. At least once chemically and at least once physically, with H bonds in the urethane segments. In the chemical crosslinking, it will be appreciated that each end of one of said plurality of urethane segments is chemically bound to one of (a) an end of one of said plurality of multi-telechelic polyisobutylene polyol segments, and (b) an end of one of said plurality of chain extender segments. Where either the polyisobutylene polyol segment or the chain extender segment is produced by a 3 or more-arm star, there is chemical crosslinking. A di-functional polyisobutylene or chain extender is not crosslinked, however.

However, there is also a physical crosslinking of the urethane segments. Thus, the invention also includes one or more of the plurality of urethane segments that are physically crosslinked to one or more other of said plurality of urethane segments.

Still another aspect of the present invention provides for a method for preparing a multiply-crosslinked polyisobutylene-based polyurethane including the steps of providing a multi-telechelic, hydroxy-terminated polyisobutylene, or a blend of a hydroxy-terminated, multi-telechelic polyisobutylene and an amine-terminated, multi-telechelic polyisbutylene; freshly distilling a diisocyanate compound to create a freshly distilled diisocyanate; reacting the multi-telechelic polyisobutylene (or blend thereof) with a stoichiometric excess of the freshly distilled diisocyanate (in the presence of a catalyst) to provide a mixture of (i) a polyisobutylene-based prepolymer terminated with isocyanate ends and (ii) diisocyanate; and adding a stoichiometric amount of a multi-functional cross-linking agent/chain extender to the mixture of the polyisobutylene-based prepolymer and diisocyanate, to charge polymerization of the prepolymer by reacting the cross-linking agent/chain extender with the diisocyanate to provide for both chemical and physical crosslinking, thereby forming the multiply-crosslinked polyisobutylene-based polyurethane. Such a polyurethane has been found to exhibit a higher creep resistance or a lower percentage of creep as compared to polyisobutylene-based polyurethane that is only physically crosslinked.

In one embodiment, the multi-telechelic polyisobutylene provided is a tri-telechelic polyisobutylene triol. In another embodiment, the multi-telechelic polyisobutylene provided is a blend of a tri-telechelic polyisobutylene triol and a di-telechelic polyisobutylene diol. All tri-telechelic polyisobutylene triol may be seen as crosslinking agents.

Thus, the embodiment where a tri-telechelic polyisobutylene triol is used, together with a stoichiometric excess of the freshly distilled diisocyanate (in the presence of a catalyst), a mixture of a polyisobutylene-based three-arm star prepolymer with three isocyanate-terminated ends and diisocyanate is provided. In the other embodiment where a blend of a tri-telechelic polyisobutylene triol and a di-telechelic polyisobutylene diol is used, together with a stoichiometric excess of the freshly distilled diisocyanate (in the presence of a catalyst), a mixture of a tri-telechelic polyisobutylene-based, three-arm star prepolymer with three isocyanate-terminated ends, a di-telechelic polyisobutylene prepolymer with two isocyanate-terminated ends, and diisocyanate is provided.

In other words, the step of reacting includes covalently bonding a terminal end of the diisocyanate to a terminal end of the multi-telechelic polyisobutylene polyol. Where the polyisobutylene polyol is polyisobutylene with 3 or more arms, the covalent bonding of the polyisobutylene to the isocyanate is a crosslink.

In one or more embodiments, the step of reacting may include reacting the multi-telechelic polyisobutylene with a stoichiometric excess of the freshly distilled diisocyanate in the presence of a catalyst. In one or more of the same or other embodiments, the step of reacting may include reacting the multi-telechelic polyisobutylene with a stoichiometric excess of the freshly distilled diisocyanate in a solvent.

In at least one embodiment, the step of adding includes adding a stoichiometric amount of a di-functional chain extender, preferably 1,4-butane diol, to the mixture of the polyisobutylene-based prepolymer and diisocyanate by reacting each end of the di-functional chain extender with either the isocyanate-terminated ends of the prepolymer or with the diisocyanate to provide a plurality of urethane groups linked to the polyisobutylene-based polymer, while also enabling the urethane groups to physically bond to each other via H bonding, thereby forming the double-crosslinked polyisobutylene-based polyurethane. That is the chain extender in this embodiment is not a crosslinking agent, and the crosslinks only occur between the 3-arm star PIBs above, and the diisocyanate, and the physical H-bonding of the resultant urethanes.

In at least another embodiment, the step of adding includes adding a stoichiometric amount of a tri-functional cross-linking agent, preferably 1,1,1-tris (hydroxymethyl) ethane (THME), to the mixture of the polyisobutylene-based prepolymer and diisocyanate by reacting each end of the tri-functional cross-linking agent with either the isocyanate-terminated ends of the prepolymer or with the diisocyanate to provide a plurality of urethane groups chemically cross-linked to the polyisobutylene-based polymer, while also enabling the urethane groups to physically bond to each other via H bonding, thereby forming the triple-crosslinked polyisobutylene-based polyurethane. That, it 3-arm short chain THME is a crosslinking agent in this embodiment, and the crosslinks occur between (1) the 3-arm star PIBs above and the diisocyanate, (2) the tri-functional crosslinking agents above and the diisocyanate, and (3) the physical H-bonding of the resultant urethanes.

To be clear, a d-functional chain extender is a chain extender in that it connects two isocyanates together, but it is not a crosslinking agent. However, a tri-functional chain extender is a crosslinking agent because it connects three isocyanates together. Thus, where "chain extender" is used, it may refer to either the di-functional chain extender such as BDO or DAB, or to all chain extenders and crosslinking agents. Where "crosslinking agent" is used in context related to a chain extender, it refers only to chain extender having 3 or more-functional groups. For purpose of this invention, the term "crosslinking agent/chain extender" refers to any multi-functional chain extender, as a di-functional chain extender is a chain extender, while everything else is a multifunctional crosslinking agent.

A further aspect of the present invention includes use of the multiply-crosslinked polyisobutylene-based polyurethane as a material of an indwelling device. In one or more embodiments, the indwelling device may be selected from the group consisting of heart valves, breast implants, synthetic ligaments, and anti-adhesion shields.

Still another aspect of the present invention includes an indwelling device comprising the multiply-crosslinked polyisobutylene-based polyurethane. In one or more embodiments, the multiply-crosslinked polyisobutylene-based polyurethane may be molded, and more specifically, reaction injection molded to form the indwelling device. In at least one embodiment, the present invention may include a heart valve comprising the multiply-crosslinked polyisobutylene-based polyurethane of the present invention.

Still other aspects of the present invention include a method for the production of an indwelling device, the method comprising molding the multiply-crosslinked polyisobutylene-based polyurethane of claim 1 into a form suitable for use as the indwelling device. In at least one embodiment, the step of molding includes reaction injection molding the multiply-crosslinked polyisobutylene-based polyurethane.

Still a further aspect of the present invention includes a heart valve comprising the multiply-crosslinked polyisobutylene-based polyurethane made by the method described above and herein.

Advantageously, the biostability and the resistance of xPIB-PU against oxidative and hydrolytic degradation is believed to be unparalleled for the fabrication of and use in indwelling devices such as heart valves. Currently, the composition of the present invention has been found to exhibit superior creep resistance as compared to PIB-PU, as well as a number of other mechanical properties.

BRIEF DESCRIPTION OF THE DRAWINGS

These and other features and advantages of the present invention will become better understood with regard to the following description, appended claims, and accompanying drawings.

DETAILED DESCRIPTION OF ILLUSTRATIVE EMBODIMENTS

Figure 1:
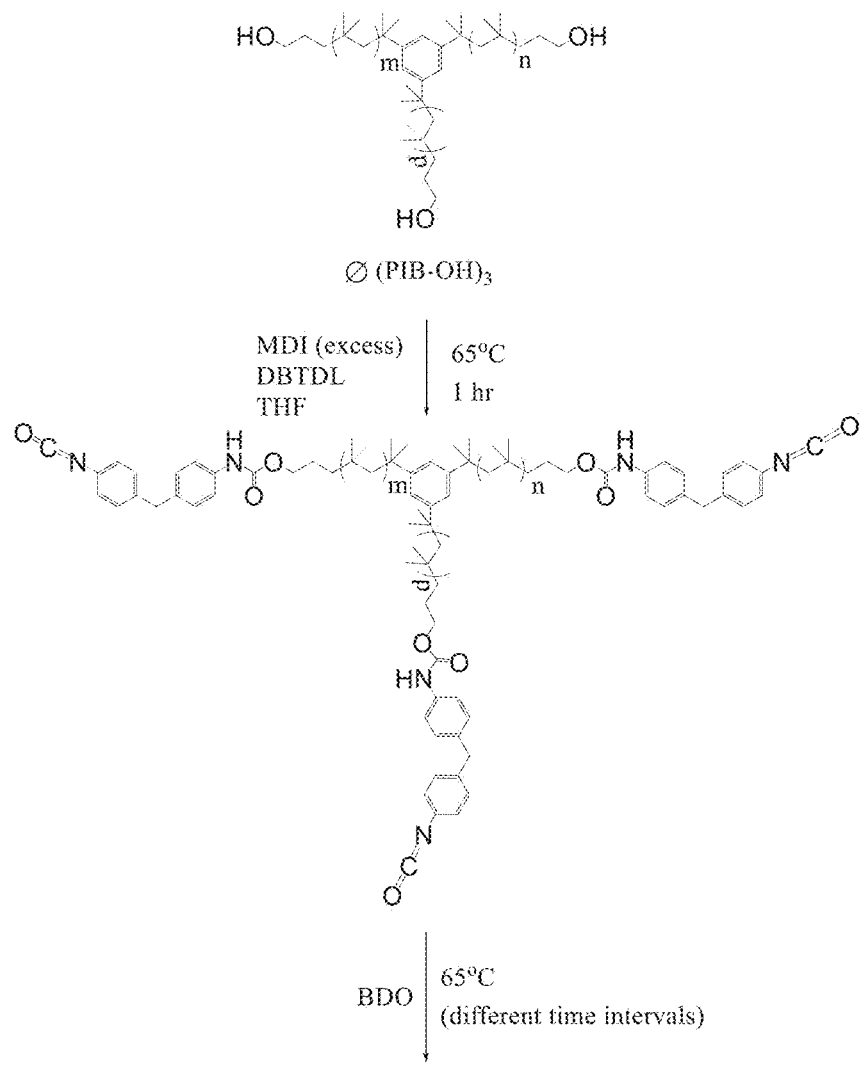
FIG. 1 is a scheme 1 synthesis and expected microarchitecture of $x_2$PIB-PU (PIB content 70 wt. %).
Figure 1:
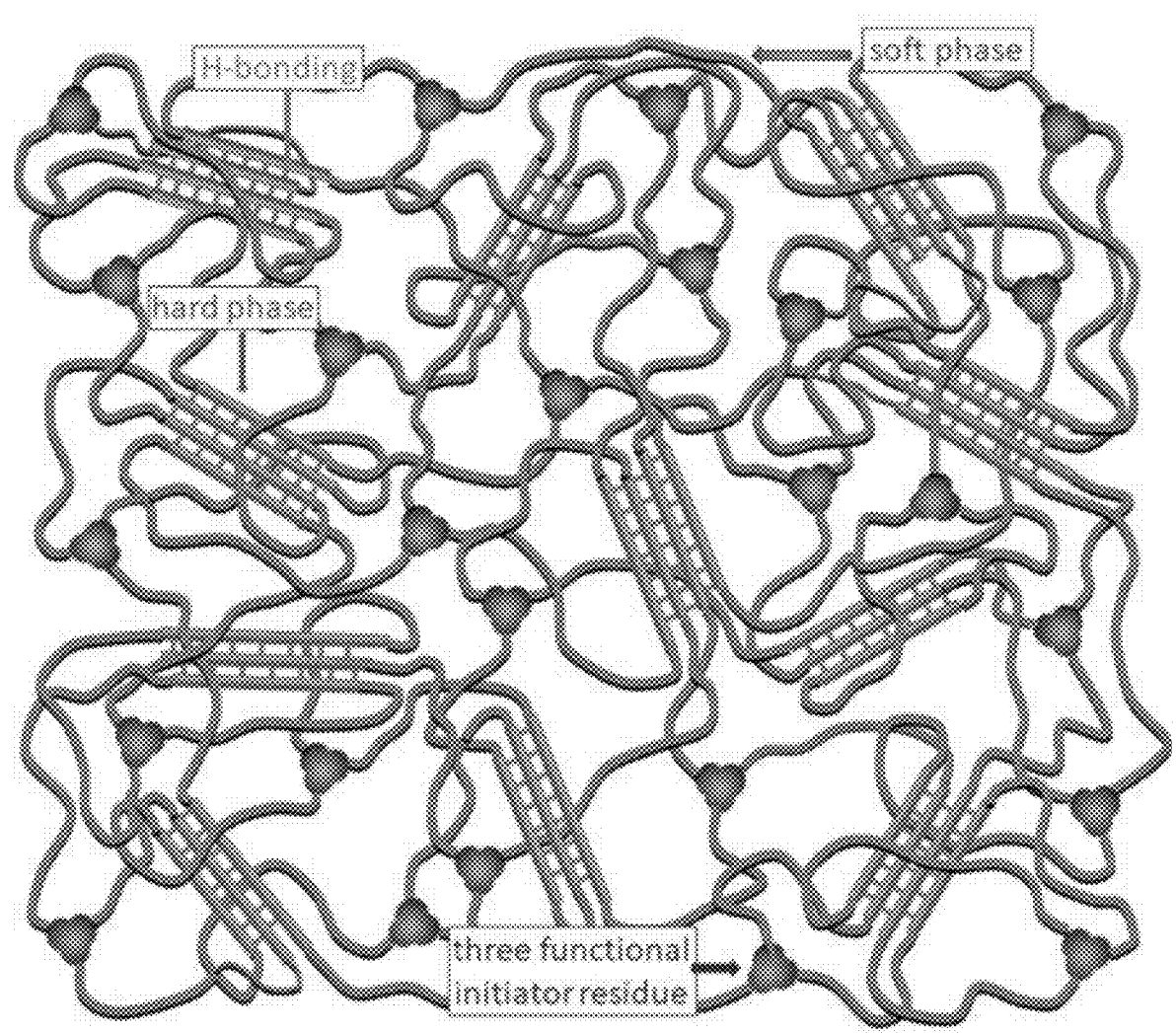

This invention relates to the preparation of well-defined elastomeric thermosets, multiply-crosslinked polyisobutylene-based polyurethanes ($x_n$PIB-PU), consisting of independently crosslinked hard polyurethane (PU) domains and soft polyisobutylene (PIB) domains that are nonetheless processible by conventional techniques. Multiply-crosslinked polyisobutylene-based polyurethanes exhibit improved properties relative to PIB-PU, for example, much increased creep resistance, toughness, etc., desirable for long-term indwelling medical devices like synthetic heart valve prostheses, orthopedic device, and anti-adhesion shields.

Before discussing the present invention, a brief overview of polyisobutylene-based polyurethanes, PIB-PUs is provided. PIB-PUs are composed of polyisobutylene soft segments (or domains) and urethane-rich hard segments (or domains) as shown below:

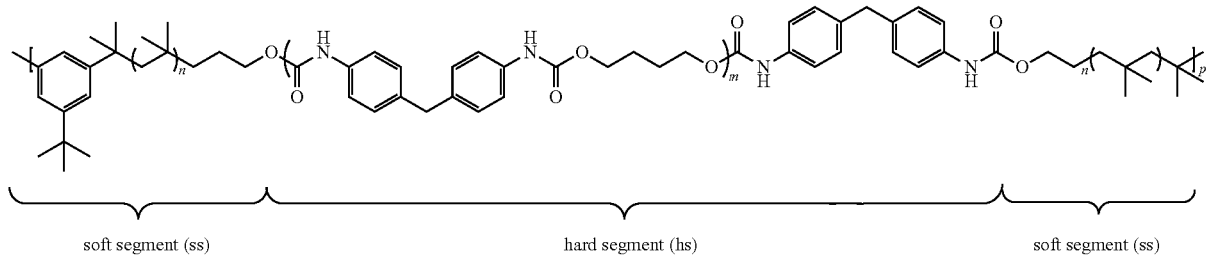

soft segment (ss)    hard segment (hs)    soft segment (ss)

The polyisobutylene chains provide tightly packed —CH$_3$ side groups protecting the surface of the PIB-PU. Similar to polysiloxane-based PUs, the —CH$_3$ groups are extremely hydrophobic barriers, forming an impenetrable shield that protects the material from hydrolytic and oxidative degradation. Unlike polysiloxane-based domains, however, the —CH$_3$ side groups of PIB-PU are closer to each other, offering better protection against hydrolytic and oxidative degradation than polysiloxane-based soft segments. Additionally, the tightly packed —CH$_3$ groups improve hemocompatibility by interrupting the adhesion of plasma platelets on the surface, hence preventing thrombosis and calcification. Polar water molecules, the most abundant ingredient of blood plasma, form a network of hydrogen bonding that defines the unique properties of water. The presence of —CH$_3$ groups on the surface of valve leaflets made of PIB-PU significantly disrupts this natural hydrogen bonded network without replacing it with an alternative hydrogen or polar bonding sites. Consequently, water molecules form a highly structured layer above the —CH$_3$ rich surface with a void domain separating them from the PIB-PU surface. For such superhydrophobic surfaces, it is believed that the plasma proteins—the precursor for platelet adhesion—either are not able to disrupt this layer to be adsorbed on the surface or they will be highly denatured if they do get adsorbed. Nevertheless, in both scenarios, platelets cannot adhere to the surface: in the former scenario, there is no plasma protein to support the adhesion of platelets, while in the latter scenario, proteins are extremely denatured and packed that cannot support the adhesion of other proteins and platelets.

As all the ingredients for PIB-PU are readily available, e.g., methylene diphenyl diisocyanate (MDI), 1,4-butanediol (BDO) (chain extender), and a catalyst, and given that is is well-known how to synthesize high number average molecular weight PIB diols (HO-PIB-OH), the key issue that has to be addressed in order to provide the best material for the proposed indwelling devices was to determine the appropriate MW that would satisfy the material requirements for such devices. That is, it is known that not all molecular weight combinations of PIB and diisocyanate will provide suitable mechanical properties. Thus, determining the level of PIB soft segments and the amount of urethane hard segments in the PIB-PU system is essential. The PIB soft segments determine the overall biostability of the PIB-PU. On the other hand, the hard segments perform a double duty: they not only physically crosslink the soft segments but also function as reinforcing filler. This filler is covalently connected to the polymer, a unique and most desirable feature. In conventional compounding of rubbers (e.g., butyl rubber, SBR rubber) the reinforcing fillers are added separately to the rubber, and reinforcement is affected by the extent of adhesion to the polymer.

Finding the appropriate molecular weights for obtaining the sought-after PIB-PU properties needed for highly demanding medical applications is a prerequisite for any material to be used in indwelling devices. It has been found that reagent purity and stoichiometry are of critical importance for the production of PIB-PU, and particularly, xPIB-PU. Generally, it has been found that any surface of PIB-PU is completely covered by —CH$_3$ groups when using about 70 wt % PIB. The about 70 wt % PIB threshold was an indicative criterion for achieving desired in vitro properties suitable for heart valve applications. For example, complete calcification resistance and excellent oxidative resistance was obtained with a minimum of 70 wt % PIB. Thus, the xPIB-PUs of the present invention should always contain at least 70 wt % PIB.

PIB model networks crosslinked with urethane chemistry, similar to PIB-PU, have been prepared previously, however, they had poor mechanical properties because the HO-PIB-OH used was made by the "inifer" technique. This technique leads to hindered end groups (i.e., —CH$_2$—CH(CH$_3$)—CH$_2$OH) whose reactivity with isocyanates is limited. Another reason these model networks lacked strength was the absence of chain extenders. PIB-PUs synthesized by living isobutylene polymerization produced unhindered end groups (i.e., —CH$_2$CH$_2$CH$_2$OH) that led to PUs with outstanding mechanical properties.

To begin, there are two key ingredients for the preparation of x$_n$PIB-PU: the PIB prepolymer and a multifunctional crosslinking agent (also termed chain extender). The PIB prepolymer (OCN-PIB-NCO) is made by reacting a PIB diol with a per-determined stoichiometric excess of diisocyanate. The number average molecular weight (Mn) of the prepolymer is generally in the 1,000 to 10,000 g/mol range. In some embodiments, the molecular weight of the prepolymer will be between 2,000 g/mol and 9,000 g/mol. In at least one embodiment, the M$_n$ of the prepolymer will be about 3,000 g/mol. In another embodiment, the M$_n$ of the prepolymer will be about 9,000 g/mol.

As conventional PIB-PU is crosslinked only by reversible physical forces (i.e., the crystalline hard domains provide crosslinking), the material may exhibit some undesirable creep particularly under permanent cyclic load. Covalent crosslinking, on the other hand, is believed to eliminate the plastic deformation of PIB-PU under cyclic loading. Thus, it was envisioned to create a unique doubly-crosslinked PIB-PU, abbreviated xPIB-PU, containing both physical-and-chemical crosslinks. A hybrid thermoplastic/thermoset, xPIB-PU exhibits a combination of properties superior to the conventional, singly-crosslinked PIB-PU, notably having negligible creep and permanent set. Chemical crosslinking was accomplished by employing a high MW trifunctional alcohol, Ø(PIB-OH)$_3$ in place of the difunctional linear diol HO-PIB-OH).

In order to create the multiply-crosslinked polyisobutylene-based polyurethanes, the PIB based prepolymer must first been prepared. Thus, a multi-telechelic PIB-based polyol is first provided. Preparation of such PIB-based polyols are well known in the art. However, one example of such a polyol suitable for use herein is a tri-functional three-arm PIB star polymer, having hydroxy (—OH) terminal ends, Ø(PIB-OH)$_3$ as set forth below.

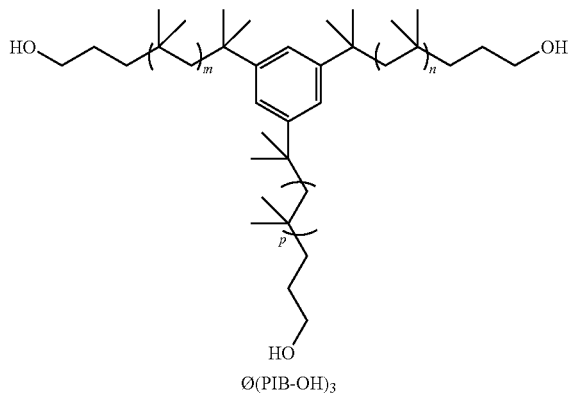

Ø(PIB-OH)$_3$

This polyol consists of three PIB arms fitted with —OH end groups, the arms emanating from an aromatic core; and m, n and p are 10 to 5,000. This polyol (a triol as shown) provides initiation for PU synthesis, the soft segment, while crosslinking the system. The enabling ingredients for the synthesis of xPIB-PUs are PIB derivatives that fulfill three essential functions simultaneously: (a) polymerization initiation, (b) providing the soft domains, and (c) crosslinking. The 3-arm star PIB with three —OH end-groups are one of the simplest representatives of such ingredients.

The present invention optimizes synthesis conditions by reacting the PIB arms with —OH end groups with an excess of freshly distilled diisocyanate such as MDI or the like, thereby increasing the mechanical properties of the resultant prepolymer.

A representative experiment used to produce the proposed prepolymer contains at least 70 wt. % PIB soft segment. As known in the art, one example of such a production is to charge a flame dried glass vial equipped with a mechanical stirrer with well dried PIB-triol, freshly distilled MDI (2.025 mmol), and distilled THF under a blanket of N$_2$. The system is stirred and heated to 65° C., then a catalyst solution (0.24 mL of a 25 mg Dibutyltin dilaurate (DBTDL)/5 mL THF) is added and stirred. Thus, a PIB-PU prepolymer is formed with excess diisocyanate remaining. Then, a butane diol or similar chain extender (dissolved in THF) is then added, and the system is further stirred.

The representative experiment discussed above discusses the use of "freshly distilled" MDI. Freshly distilled within the context of this application means that the MDI was distilled and then used within 1 to 2 hours after distillation to create the prepolymer of the present invention. Freshly distilled further defines that the freshly distilled MDI was not stored prior to being used to create the xPIB-PU's of the present invention.

Although the above experiment discusses the use of DBTDL as the catalyst, in other embodiments of the present invention, other catalysts could be used such as stannous octoate, bismuth/zinc, zirconium and bismuth organics including bismuth neodecanoate, zinc neodecanoate, zinc carboxylate, and bismuth carboxylate, vanadium organics, and cobalt organics.

As stated above, it was determined that the purity of the MDI utilized to create the PIB-PU's of the present invention was vital to the advanced mechanical properties of the produced.

Non-polyisobutylene-based low molecular weight multifunctional alcohol crosslinking agents/chain extenders are, for example, 1,4-butane diol (BDO), 2-hydroxymethyl-1 3-propanediol, 1,1,1-tris(hydroxymethyl)ethane (THME), and 1,1,1-tris(hydroxymethyl)propane (THMP). Low molecular weight multifunctional amine crosslinking agents/chain extenders are, for example, 1,4-diaminobutane (DAB) and Tris(2-aminoethyl)amine (TAEA).

The other ingredients needed for the preparation of x$_2$PIB-PUs (i.e., MDI, BDO) are well-known and have been described.

The synthesis and characterization of Ø(PIB-OH)$_3$, i.e., the three-arm star PIB fitted with —OH end groups, has been described, however, we are unaware of its use as a crosslinking agent for the preparation of crosslinked PIB-PU. While urethane bond formation between the prepolymer and Ø(PIB-OH)$_3$ was expected (see FIG. 1, Scheme 1), the practical consequences caused by the molecular weights of the crosslinking agent on processability time were unexpected. Experimentally we found that to prepare crosslinked PIB-PU with 70 wt. % PIB the number average molecular weight of the crosslinking agent, the PIB segment, must be in the 3,000-10,000 g/mole range.

Further, we have shown that the processability period of crosslinked PIB-PU can be controlled by blends of crosslinking agents; for example, using blends of Ø(PIB-OH)$_3$ and OH-ditelechelic PIBs, having well-defined molecular weights. In some embodiments where such blends are used, the blend may be from 10% to 90% by weight of the three-arm PIB and from 90% to 10% by weight of the two-arm PIB. In other embodiments, from 20% to 75% of the three-arm PIB may be blended with 80% to 25% of the two-arm PIB. It is noted that, generally, use of blends in these ratios will provide for cross-linking.

However, in some embodiments, up to 25% by weight, more preferably, between 10% to 25% by weight of the Ø(PIB-OH)$_3$ may be used, and at least 75% by weight, and more preferably, between 75% to 90% by weight of the di-telechelic PIB may be used. It will be understood that in these embodiments, there is not complete crosslinking. Instead, what is provided is a hyperbranched prepolymer that is soluble in THF. It will be appreciated that for purposes of this invention, any claim or portion of a claim directed to crosslinking or a crosslinked polyurethane that includes a three-arm PIB in any amount, even in a blend with a two-arm PIB, will still be considered a part of the invention inasmuch as a three-arm (or multi-arm PIB) is used in the preparation of the polyurethane.

Notably, the more tri-telechelic PIB used, the faster and stronger the polymer will be crosslinked. Use of tri-telechelic PIB or higher arm start polymers of PIB will result in crosslinking immediately. In some embodiments, given that for production of some articles of manufacture, gel formation times are important, a blend of tri-telechelic PIB and di-telechelic PIB blends provide a feasible alternative to a system that is entirely crosslinked.

Where the multi-arm PIBs create cross-links, it will be appreciated that the resultant xPIB-PUs will have a higher Young's modulus that with other PIB-PUs or even other xPIB-PU that do not solely use multi-arm PIBs. Again, where multi-arm PIB is used, it is preferred that the molecular weight be between 3,000 g/mole and 10,000 g/mole.

It will also be appreciated that crosslinked PIB-PU can also be created by using multi-arm crosslinking agents. Examples of such suitable crosslinking agents include

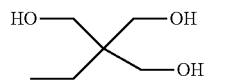

1,1,1-Tris (hydroxymethyl) propane
(THMP)

1,1,1-Tris (hydroxymethyl) ethane
(THME)

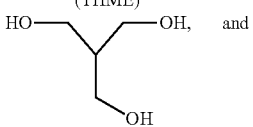

2-Hydroxymethyl-1,3-propanediol
(Trimetylolmethane)
(TMolM)

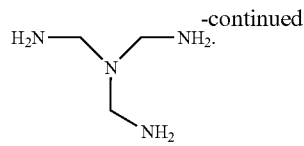

Tris(2-aminoethyl) amine
(TAEA)

Where tri-telechelic, low molecular weight crosslinkers are employed, the resultant network is more bound, and exhibit higher elongation properties. Thus, in some embodiments, only a di-telechelic chain extender such as 1,4-butanediol (BDO) or diaminobutane (DAB) are used. There is not crosslinking of the chain extender in these embodiments. In other embodiments, only a tri-telechelic crosslinking agents/chain extender such as TMHP, THME, TMolM, or TAEA are used. In still other embodiments, blends of di-telechelic and tri-telechelic chain extenders may be used. Generally, it has been found that where tri-telechelic crosslinkers are used, the molecular weight of the PIB segment should be closer to 3,000 g/mol in the 3,000 g/mol to 10,000 g/mol range.

Where blends of a di-telechelic chain extender and a tri-telechelic crosslinker is used, the blend may be from 10% to 90% by weight of the tri-telechelic crosslinker and from 90% to 10% by weight of the di-telechelic chain extender. In other embodiments, from 20% to 75% of the tri-telechelic crosslinker may be blended with 80% to 25% of the di-telechelic chain extender. It is noted that, generally, use of blends in these ratios will provide for cross-linking.

Where tri-telechelic chain extenders are used, crosslinking occurs, it will be appreciated that the resultant xPIB-PUs will have a higher elongation than with other PIB-PUs or even other xPIB-PU that do not solely use such chain extenders.

With respect to the use of hydroxy-terminated chain extenders and amine-terminated chain extenders, it will be appreciated that at least some hydroxy-terminated chain extenders are preferred, because if all amine-terminated chain extenders are used, then they react too fast to permit gel formation and molding. We are unaware of disclosures reading on materials prepared with blends of two well-defined molecular weight crosslinking agents In the present invention, it is envisioned that the crosslinked polyurethane can be employed in reaction injection molding apparatuses to produce various articles of manufacture including heart valves and other indwelling devices. In the reaction injection molding (RIM) process, two hot streams under high pressure (200 psi-14 atm) and high temperatures (up to 180° C.) may be used to produce the xPIB PUs. The first stream contains the stoichiometric mixture of either MDI (diisocyanate) and multi-hydroxy telechelic polyisobutylene [Ø(PIB-OH)$_3$] or MDI (diisocyanate) and multi-hydroxy telechelic polyisobutylene [Ø(PIB-OH)$_2$] while the second stream contains either BDO chain extender or a mixture of multi-hydroxy (or multiamine)/BDO (1,4-diaminobutane) extenders. These two streams are combined in a mixing chamber, resulting in the production of crosslinked polyurethanes.

The rate of laminar flow of the these ingredients into the mixing chamber must satisfy the stoichiometry of polyurethane formation, i.e., the molar concentration of isocyanate groups must be equal to that of the molar concentration of alcohol groups. The best mechanical properties can be obtained when the MW of the PIB moiety is in the 3000-10,000 g/mol range. Finally, the molten polyurethane mass in the mixing chamber is propelled under high pressure into the heated mold. Experiments carried out in the presence of crosslinking agents produce crosslinked products of the desired shape. After cooling the mold, the final article is recovered.

Preparation and Structure of Multiply-Crosslinked Polyisobutylene-Based Polyurethane The details of the synthesis of processible multiply-crosslinked polyisobutylene-based polyurethane are critical. The process starts by preparing a prepolymer by mixing the calculated amount of crosslinking agent, say Ø(PIB-OH)$_3$, with a slight molar excess of MDI (in the presence of a well-known catalyst, for example, dibutyl tin laureate, DBDTL), and subsequently adding the stoichiometric amount of chain extender (e.g., 1,4-butane diol (BDO)) to start the step growth polymerization of polyurethane. The stoichiometry of the functional groups (i.e., the molecular weight of the prepolymer and chain extender) must be carefully controlled, such that upon initial reaction between the hydroxy-terminated PIB and diisocyanate, a polyurethane prepolymer is formed and excess diisocyanate remains. Then, the chain extender (BDO) is added. FIG. 1 shows the scheme 1 for this and helps to visualize the process and shows the idealized structure of x$_2$PIB-PU.

A comparison of the architectures of this twice-crosslinked (with H bonds and Ø(PIB-OH)$_3$) and the earlier mono-crosslinked (with only H bonds) PIB-PU shows a variety of significant differences, which helps to understand the macroscopic differences in the properties of these hybrid structures. First, the permanent crosslinks introduced by the crosslinking agent lead to significantly improved creep resistance. These permanent crosslinks also lead to enhanced branching, chain entanglements, reduction in chain mobility, catenations, etc., in the PIB domains, which are expected to increase, toughness, density, hardness, and reduction of elongation. The permanent crosslinks will also lead to improved durability and fatigue properties, as well as crack initiation and propagation rates. The examination of the effect of enhanced crosslink density on properties will provide valuable insight into the structure/property relationship of these polymers.

Processability, Gel Time and Pour Time

Experimentally, the charge producing crosslinked PIB-PU is processible (i.e., stirrable, pourable, miscible, etc.) during the period starting with the addition of the chain extender (BDO), and remains processible until the increasing viscosity (i.e., growing molecular weight) of the charge prevents stirring. The length of this processability period can be controlled by controlling the molecular weight of the crosslinking agent keeping the weight % of the soft domain constant. If the molecular weight of the crosslinking agent is too low (i.e., if m, n, and p are zero or very low) highly branched and tightly crosslinked x$_2$PIB-PU quickly forms and the processing period will be too short for practical use. And if the molecular weight of the crosslinking agent is too high x$_2$PIB-PU will form very slowly or may not even occur within a practically reasonable length of time (few hours). In other words, the length of the processability period depends on the molecular weight of the crosslinking agent [Ø(PIB-OH)$_3$], or, more precisely, it is controlled by the contribution of the functional groups of Ø(PIB-OH)$_3$ to the average functionality of the reaction mixture. If the average functionality of the reaction mixture is high (>>2) the rate of crosslinking will be high and the processability period may be too short or practically absent; conversely, if it is low (only slightly higher than 2) crosslinking may be too slow or will not even occur within a reasonable time (few hours).

We studied the lengths of the processability period using Mn of Ø(PIB-OH)$_3$=3,000 and 9,000 g/mole. During the synthesis the viscosity of the stirred systems increased at first slowly and later more rapidly, indicating molecular weight growth. The completion of crosslinking at the gel point (i.e., reaching the maximum molecular weight, or the formation of one single giant insoluble molecule), was indicated by sudden massive polymer precipitation that stopped stirring. This phenomenon that crosslinkable polymer systems have a sharply defined gel point at a critical extent of reaction is well known. We call the time to reach the gel point "gel time" and use it to indicate the end (length) of the processability period. We found in several repeat experiments using the Ø(PIB-OH)$_3$ of Mn=3,018 g/mole that the gel time was 7.6-8 mins. (see Example 1).

Since the molecular weight of gels formed cannot be measured, we approximated gel times by determining "pour times", i.e., the maximum length of time the system is still pourable (processible), since the molecular weight of the product at pour time can be easily measured (for example by GPC). Pour times are readily identifiable by observing a reduced rate of stirring. We found both gel times and pour times quite reproducible (fractions of minutes).

Controlling the Processability Period by Controlling the Molecular Weight of the Crosslinking Agent Based on the mechanism of polyurethane step growth polymerization (see Scheme 1) and on Carothers' and Flory's teachings in respect to gelation, we carried out experiments and calculations for obtaining convenient processability periods.

In step growth polymerization linear chain growth and crosslinked product (gel) formation are determined by the average monomer functionality $f_{avg}$ of the charge:

$$f_{avg} = \Sigma n_i f_i \qquad (1)$$

where $n_i$ is the mole fraction of monomer i with functionality $f_i$. And the average degree of polymerization ($DP_n$) is:

$$DP_n = 2/(2 - f_{avg} p) \qquad (2)$$

where p is the extent of reaction as the fraction of functional groups that reacted. If $f_{avg}$=2, a linear polymer is obtained, and if p=1, $DP_n$ will be theoretically infinite (complete conversion of functional groups). If $f_{avg}$>2, branched/crosslinked systems are obtained. Thus, if p is less than one, $DP_n$ as a function of average functionality ($f_{avg}$) will also be infinite, indicating crosslinked polymer formation. $DP_n$ to be infinite, the denominator of equation 2 must be zero. Thus, if 2−$f_{avg}$ p is zero and favg of the monomer mixture is known, the required p for infinite DPn can be calculated.

In all experiments we aimed to produce x2PIB-PU with 70 wt. % polyisobutylene-based (for biocompatibility). And in all our calculations the molar concentration of —OH and —NCO groups were equal, i.e., n Ø(PIB-OH)$_3$+n BDO=n MDI.

EXAMPLES

We performed several experiments. In Example 1 we used Ø(PIB-OH)$_3$ of MW=3018 g/mole and calculated the extent of reaction (p) of functional groups at gel time. The measured gel time was 8 mins.

Thus, by using n Ø(PIB-OH)$_3$=0.1136 mmole, n BDO=0.3572 mmole and n MDI=0.4708 mmole, $$f_{avg} = \frac{n\emptyset(PIB\text{-}OH)_3 \times 3 + n\ BDO \times 2 + n\ MDI \times 2}{n\emptyset(PIB\text{-}OH)_3 + n\ BDO + n\ MDI} = 2.121$$

And according to the above-mentioned approximation the calculated extent of reaction at gel time was 0.919.

Experiment 2 was carried out under identical conditions except the molecular weight of Ø(PIB-OH)$_3$ was 9,000 g/mole. In this case the experimentally observed gel time was 41 mins and the calculated extent of reaction p was 0.980.

After these experiments we calculated the gel times and p's for systems in which the molecular weights of Ø(PIB-OH)$_3$ were 6,000 and 4,00 g/mole. These molecular weights were selected to be between the experimental molecular weights so we could see the trends for gel time and p. The calculated results were as follows: With the 6,000 g/mole crosslinking agent gel time was 32 minutes at p=0.969; and with the 4,000 g/mole crosslinker gel time was 18 minutes at p=0.954.

Figure 2:
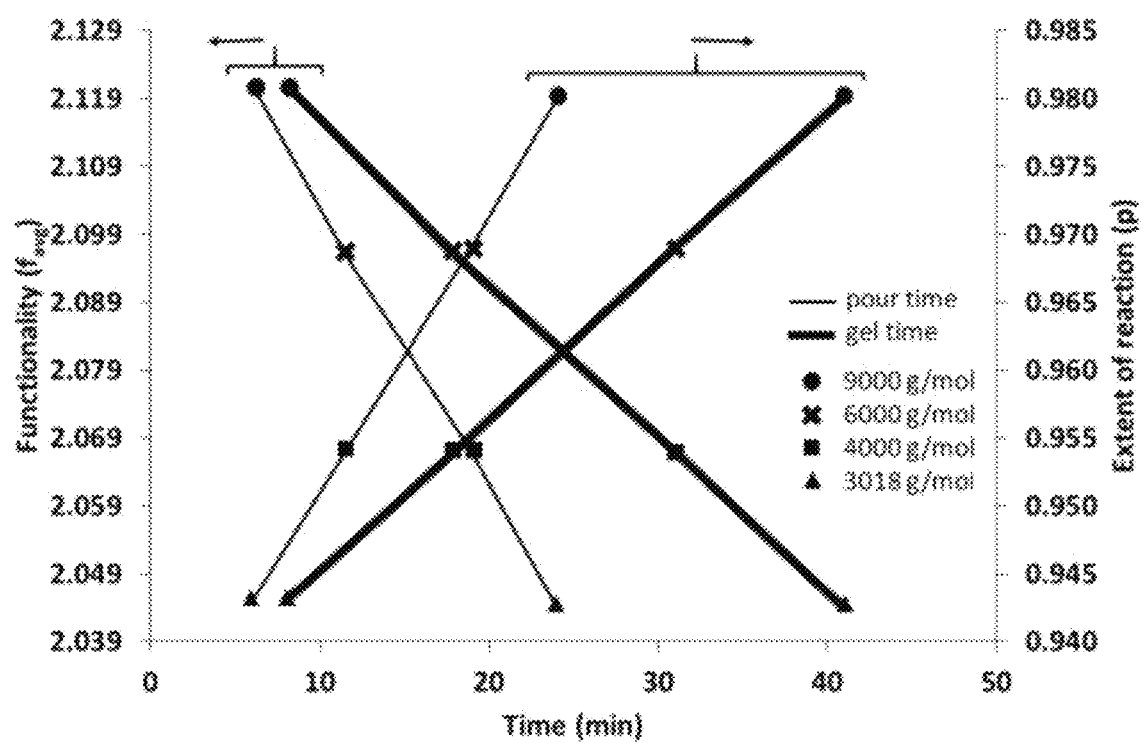
FIG. 2 is a graph plotting gel times and pour time as a function of $f_{avg}$ and p using various molecular weights of Ø(PIB-OH)$_3$.

According to these studies gel times increase with the molecular weight of Ø(PIB-OH)$_3$, indicating that the processability period increases with the molecular weight of the crosslinking agent. Table 1 and FIG. 2 summarize the experimental and calculated data. Table 1. Summary of experimental and calculated data showing the effect of molecular weights of Ø(PIB-OH)$_3$, f$_{avg}$, and extent of reaction (p), on gel and pour times.

TABLE 1

Summary of experimental and calculated data showing the effect of molecular weights of Ø(PIB—OH)$_3$, f$_{avg}$, and extent of reaction (p), on gel and pour times.

| | MW Ø (PIB—OH)$_3$ (g/mole) | f$_{avg}$ | p | pour time (min) | gel time (min) |
|---|---|---|---|---|---|
| 1 | 3,081 | 2.121 | 0.943 | 6 | 8 |
| 2* | 4,000 | 2.096 | 0.954 | 12 | 18 |
| 3* | 6,000 | 2.065 | 0.969 | 19 | 31 |
| 4 | 9,000 | 2.044 | 0.980 | 24 | 41 |

*calculated data

Unexpectedly, the two calculated data points (i.e., for Ø(PIB-OH)$_3$=4,000 and 6,000 g/mole) inserted between the two experimental data points (see FIG. 2) indicated a linear relationship between f$_{avg}$ and time, and p and time. This is evidence that the processability period increases linearly and very rapidly with even a small increase in p, and that the processability period can be effectively controlled by controlling the molecular weight of the crosslinking agent.

Gel Time Determination

Crosslinked PIB-PU syntheses were carried out in a flame dried 20 mL vial closed by a rubber septum and carrying a small condenser. Calculated amounts of Ø(PIB-OH)$_3$ (0.35 g, 0.114 mmole) and MDI (117.9 mg, 0.471 mmole) were weighted into the dry vial. The vial was degassed under reduced pressure and charged again with dry nitrogen gas. Then, 2.0 mL THF was transferred into the vial via syringe under N$_2$ atmosphere to dissolve the charge. After the addition of DBTDL catalyst solution in THF (0.8 mg, 0.0013 mmole-0.4 mL of 2.0 mg/mL), the vial was placed in an oil bath at 65° C. and the mixture was stirred for 1 hour to form the prepolymer. Separately, BDO (32.7 mg, 0.357 mmole) was weighed in another flame dried vial closed by a rubber septum. The vial was evacuated at 2.0×10$^{-2}$ mm Hg and charged with gaseous N$_2$ and 2.0 mL dry THF added by a syringe under N$_2$ atmosphere. Then the BDO solution was transferred to the vial with the prepolymer by a steel cannula. The viscosity increase became visible in five minutes. Then, 8 minutes after the addition of the BDO chain extender stirring suddenly stopped because the high viscosity prevented further stirring. Thus, the gel time, i.e., the processability period, was 8 minutes.

Processability Demonstration

Following the procedure described in Example 1 we prepared a prepolymer solution and induced the formation of x2PIB-PU by the addition of BDO chain extender. As observed previously, the viscosity of the system started to rise soon after BDO addition. The content of the vial (Ø(PIB-OH)$_3$-3,000 g/mole, 6 minutes) was immediately poured into a 7 x7×0.3 cm glass mold and covered by a glass plate, leaving a small opening to allow the THF to escape. The system was placed in a vacuum oven and heated at 65° C. for 3 days. After cooling the system to room temperature and removing the glass cover an optically clear strong rubbery film was obtained. A small sample was removed from the rubbery film and placed in THF. The film swelled but did not dissolve after several days in THF indicating that it was crosslinked.

Moreover, Soxhlet extraction was used to separate possible soluble fractions in x2PIB-PU. A sample of x2PIB-PU film (1×1 cm) of constant weight was placed into the apparatus. The reflux process was conducted for 12 hours by THF as a solvent. Then, the insoluble film was dried to constant weight in a vacuum oven for three days at 65° C. As a result, a 2.7% soluble fraction was detected by gravimetric analysis. In view of the very low amount of the soluble fraction, the sample was highly crosslinked.

Crosslinking with Blends of Linear Plus Branched Crosslinkers

The length of the processability period of crosslinked PIB-PU can be controlled by the nature and molar concentration of the functional end groups. A further effective way to produce crosslinked PIB-PU is by using blends of linear telechelic PIB diols, for example:

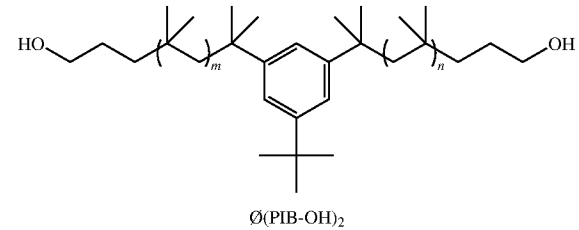

Ø(PIB-OH)$_2$ plus 3 arm star telechelic polyisobutylene-based triols as crosslinking agents. (Note that the telechelic diol was abbreviated by the symbol HO-PIB-OH in earlier references)

In view of the great structural similarity of Ø(PIB-OH)$_3$ and Ø(PIB-OH)$_2$, we expected no difficulty homogeneous blending these molecules for the synthesis of x2PIB-PU. As Ø(PIB)$_3$ and Ø(PIB-OH)$_2$ are thermodynamically compatible their blends indeed gave homogeneous solutions.

Figure 3:
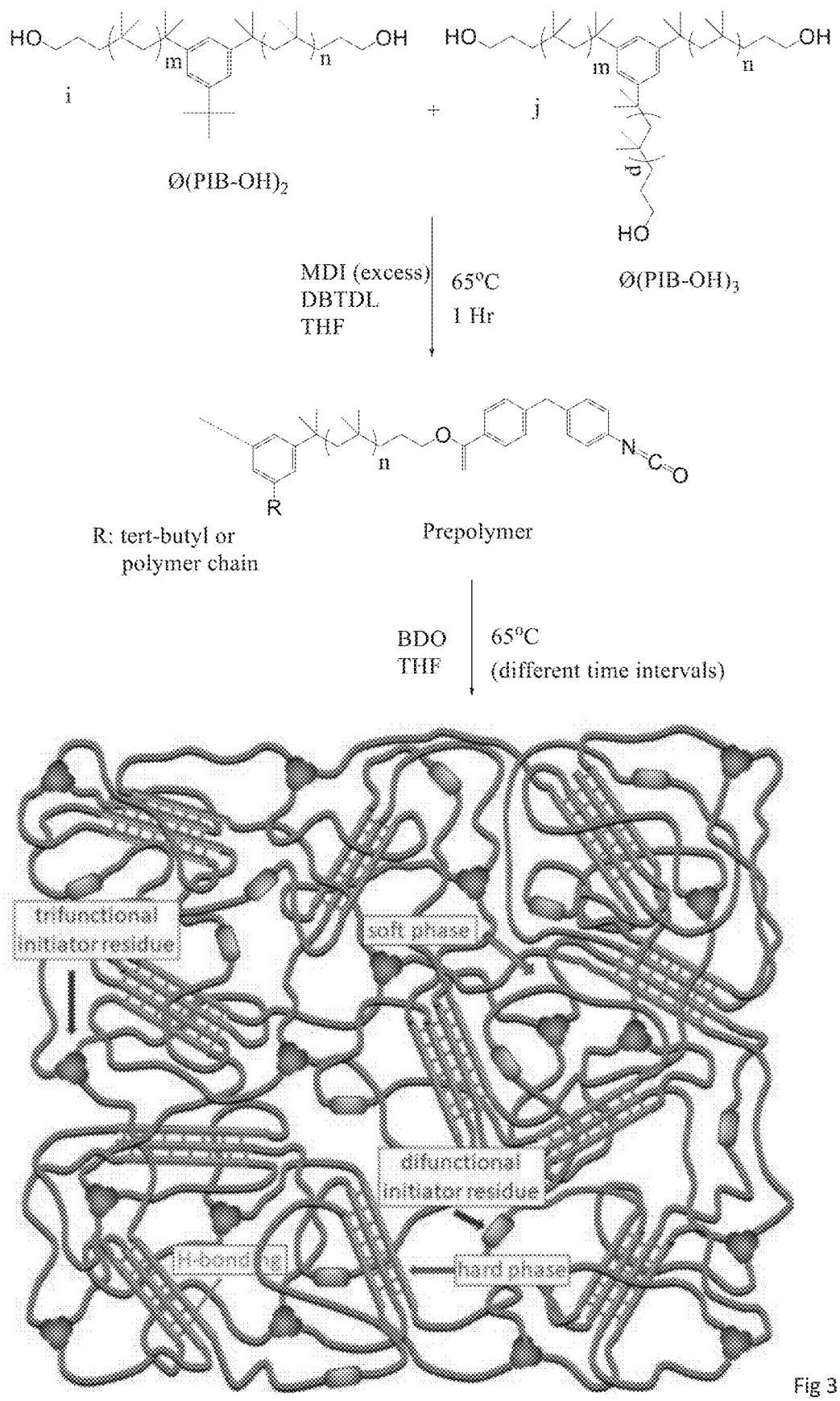
FIG. 3 is a scheme 2 synthesis of xPIB-PU with blends of linear telechelic diols and 3-arm star telcechelic PIB triols (the soft domain is ~70 wt. %).

FIG. 3, scheme 2, outlines the synthesis of x2PIB-PU using blends of Ø(PIB-OH)$_3$ plus Ø(PIB-OH)$_2$ and shows the microarchitecture of the final product.

An embodiment of the invention is controlling (increasing) the length of the processability period by reducing the relative concentration of the Ø(PIB-OH)$_3$ crosslinking agent by adding the linear diol. By lowering the Ø(PIB-OH)$_3$ concentrations, the rate of molecular weight growth and the rate of crosslinking are reduced. Delayed crosslinking increases the time during which the system is processible, i.e., reducing the relative concentration of Ø(PIB-OH)$_3$ reduces the rate of crosslinking and increases the processability period.

An embodiment of the invention is controlling (increasing) the length of the processability period by reducing the relative concentration of the Ø(PIB-OH)$_3$ crosslinking agent by adding the linear diol. By lowering the Ø(PIB-OH)$_3$ concentrations, the rate of molecular weight growth and the rate of crosslinking are reduced. Delayed crosslinking increases the time during which the system is processible, i.e., reducing the relative concentration of Ø(PIB-OH)$_3$ reduces the rate of crosslinking and increases the processability period.

This method produces a new type of composition of matter in which the soft PIB domain is a blend of linear and 3-arm star crosslinkers.

Experiments were carried out in which we prepared crosslinked PIB-PUs whose soft domains were homogeneous blends of linear and 3-arm PIBs, and the hard domains were of conventional MDI and BDO. Experimental details were the same as those used for the synthesis of PIB-PU, except a blend of linear and 3-arm star crosslinking agents was used. FIG. 3, scheme 2, helps to visualize the synthesis of crosslinked PIB-PU and the structure of the target product.

These experiments were developed in two ways. In the first group the amounts of ingredients were controlled to give slow crosslinking (90 and 80 mole % crosslinking agent: ø(PIB-OH)$_3$/ø(PIB-OH)$_2$+ø(PIB-OH)$_3$), and a crosslinked PIB-PU with 70 wt. % soft segment for biocompatibility.

Thus, in a 50 mL glass vial containing a Teflon-coated ~2 cm stirring bar and sealed with a rubber septum were placed 6 mL THF, and the ingredients for the prepolymerization of PIB-PU containing 70 wt % PIB (90% ø(PIB-OH)$_3$): 50.5 mg (13.0×10$^{-2}$ mmole) Ø(PIB-OH)$_2$ of Mn=4000 g/mole, 350.0 mg (11.4×10$^{-2}$ mmole) Ø(PIB-OH)$_3$ of Mn=3081 g/mole and 138.3 mg (55.3×10$^{-2}$ mmole) MDI. The temperature was increased to 65° C. to ensure mixing thoroughly and then 0.2 mL DBTDL solution (8 mg DBTDL/5 mL THF) solution was added. Prepolymerization was conducted for 1 hour and 33.3 mg (35.4×10$^{-2}$ mmole) BDO was transferred to the vial by using a stainless-steel cannula under N$_2$ atmosphere. The charge was stirred at 65° C., and visual observations were made every ~1 mins. About 9.5 minutes after BDO addition the magnetic stir bar rotation became very difficult and stopped completely in the 10th minute. This time was taken as the gel time.

When this experiment was repeated using 80% Ø(PIB-OH)$_3$ and 20% Ø(PIB-OH)$_2$, the gel time was 40 minutes. As stated above, the gel time was 8 minutes when Mn of Ø(PIB-OH)3=3000 g/mole used alone as soft segment. These results clearly show that reducing the relative concentration of Ø(PIB-OH)$_3$ reduces the rate of crosslinking and increases the processability period.

TABLE 2

Synthesis of x2PIB—PU using a blend of Ø(PIB—OH)$_3$ plus Ø(PIB—OH)$_2$ [Ø(PIB—OH)$_2$ is minor amount].

| No. | MW Ø(PIB—OH)$_3$ (3,018 g/mole) mole % | MW Ø(PIB—OH)$_2$ (4,000 g/mole) mole % | Gel time (min) |
|---|---|---|---|
| 1 | 90 | 10 | 10 |
| 2 | 80 | 20 | 40 |

The procedure used in the first group of experiments was also applied in the second group where ø(PIB-OH)$_3$ is the minor amount. So that, the amounts of ingredients were controlled to give slow crosslinking or branching (2, 4, 8, 15 mole % crosslinking agent: ø(PIB-OH)$_3$/ø(PIB-OH)$_2$+ø(PIB-OH)$_3$), and a crosslinked polyisobutylene-based polyurethane with 70 wt % soft segment. The results are summarized in Table 3. In these experiments were performed by adding 2 to 15% ø(PIB-OH)$_2$ to the ø(PIB-OH)$_3$/ø(PIB-OH)$_2$ mixture, although increase in viscosity was observed in three hours, gel formation did not occur.

TABLE 3

Synthesis of x2PIB—PU using a blend of Ø(PIB—OH)$_3$ plus Ø(PIB—OH)$_2$ [Ø(PIB—OH)$_3$ in minor amount]

| No. | MW Ø(PIB—OH)$_3$ (3,018 g/mole) mole % | MW Ø(PIB—OH)$_2$ (4,000 g/mole) mole % | gelation |
|---|---|---|---|
| 1 | 2 | 98 | no |
| 2 | 4 | 96 | no |
| 3 | 8 | 92 | no |
| 4 | 15 | 85 | very high viscosity |

Crosslinking Width Multifunctional Amines

Crosslinking with multifunctional alcohols were discussed above. Similar embodiments concern synthesis with multifunctional amines, e.g., tris(2-aminoethyl) amine [HC(CH$_2$CH$_2$—NH$_2$)$_3$], triethanolamine, tris-(2-aminoethyl) amine.

Amine-crosslinked products introduce urea linkages (—NH—CO—NH—) into the hard segments of the polyisobutylene-based polyurethane molecule. Thus, these materials possess three kinds of crosslinks (x3PIb-PU): 1) the multifunctional polyisobutylene-based alcohol that crosslinks the soft segments, 2) the numerous H bonds that crosslink the hard segments, and 3) the multifunctional amines that also crosslink the hard segments. The number of functionalities and the molecular weights of the multifunctional compounds can be controlled, which enables the controlling of the mechanical properties of these x3PIB-PU molecules. We started to explore the effect of the lowest molecular weights of three functional crosslinking agents.

The great advantage of urea linkages is that they form rapidly in the absence of catalyst, and that they are stronger than urethane linkages (—NH—COO—). The following chemical equations help to visualize the synthesis of these poly(urethane-urea) hybrids and their microarchitecture.

Creep Studies

Creep is the tendency of a material to deform permanently under stress. Creep experiments were performed with a dynamic mechanical analyzer (DMA-Q800, TA Instruments) by applying 1 MPa constant shear stress and measuring time-dependent deformation in terms of creep strain.

Permanent deformation was measured by isothermal creep test under constant stress for 15 minutes at 25° C., followed by recovery for 25 minutes.

Figure 4:
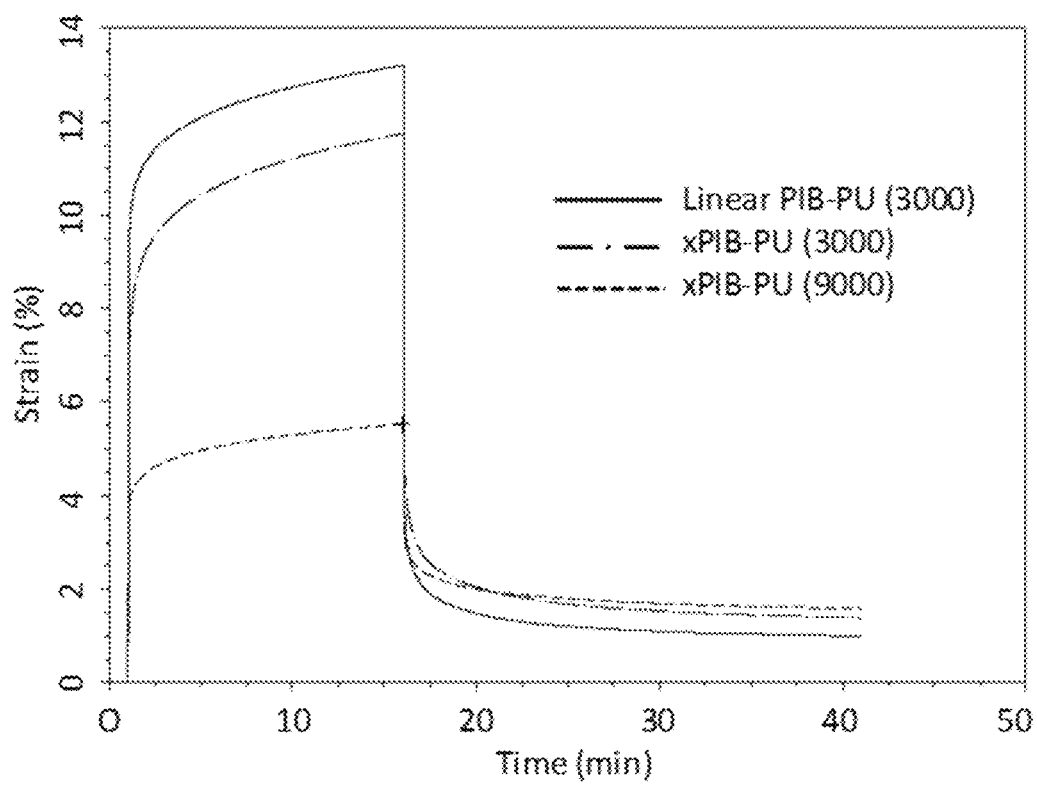
FIG. 4 is a graph of creep strain versus time.

FIG. 4 shows creep strain versus time profile of PIB-PU (3,000 g/mole), crosslinked PIB-PU (3,018 g/mole) and crosslinked PIB-PU (9,000 g/mole). The results are summarized in Table 4.

TABLE 4

Creep strain and permanent set of PIB—PU (3,000 g/mole), crosslinked PIB—PU (3,018 g/mole) and crosslinked PIB—PU (9,000 g/mole).

| Sample (Mn, g/mole | Strain (%) | Permanent set (%) |
|---|---|---|
| PIB—PU (30,00) | 13.2 | 1.0 |
| xPIB—PU (3,018) | 11.7 | 1.4 |
| xPIB—PU (9,000) | 5.5 | 1.6 |

As expected, crosslinking strongly affects creep strain. Evidently, the restricted molecular motions of the network reduce creep strain. The xcPIB-PU with the higher molecular weight crosslinking agent (9,000 g/mole) leads to higher creep resistance than the crosslinked PIB-PU with the lower (3,000 g/mole) molecular weight crosslinker. This effect may be due to the lower extent of deformation (more room) when the higher molecular weight crosslinker is used (i.e., there is more space available for aligning the crystalline phase). The shorter crosslinker (3,000 g/mole), likely prevents the formation of crystalline domains by steric hindrance. The restricted formation of crystalline phases also results in slightly higher permanent sets most probably due to the higher plasticity. However, all three samples exhibited very similar low permanent sets in the 1.0-1.5% range.

Tensile Properties

Figure 5:
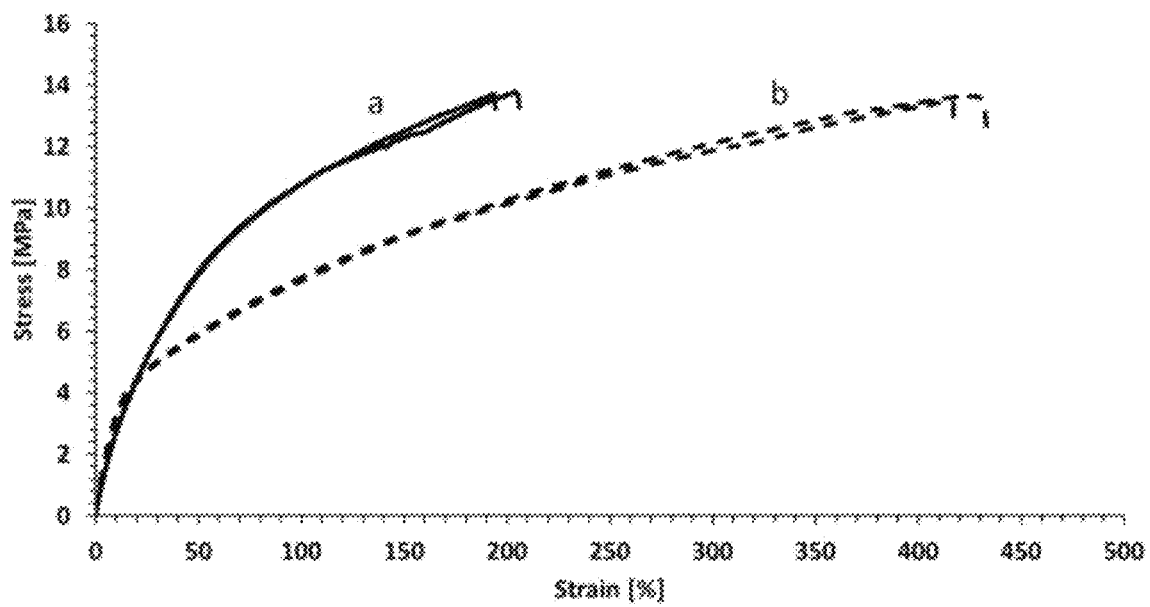
FIG. 5 is a graph showing stress-strain traces of xPIB-PU prepared (a) with 3,018, and (b) 9,000 g/mole crosslinking agent.

Stress-strain behavior was determined by an Instron model 5567 Universal Tester. A bench top die was used to cut 30×3.5×0.2 mm dogbones from cast films. Samples were tested to failure at a crosshead speed of 50 mm/min at room temperature. Averages of two sets of measurements are reported (FIG. 5, Table 5).

Young's modulus is a measure of the resistance of material to elastic deformation under load. A material whose Young's modulus is high resists more initial force, even under repeated applied loads and releases it without permanent deformation. A low modulus polymer would be less resistant. Young's moduli of crosslinked PIB-PU prepared with MW=3,018 and 9,000 g/mole crosslinking agents are 31.0 and 42.0 MPa, respectively. These moduli are much higher than those of earlier PIB-PUs (16.0 MPa). In spite of the high Young's moduli, both crosslinked PIB-PUs were unexpectedly supple and flexible. The crosslinked PIB-PU prepared with the 9,000 g/mole crosslinking agent showed remarkably high strain at break (425%). The lower strain (~200%) exhibited by the crosslinked PIB-PU prepared with 3,018 g/mole crosslinker is most likely due to the low molecular weights between crosslinks (MW~1,000 g/mole).

In view of our creep studies, it is not surprising that the crosslinked PIB-PU (9,000 g/mole) specimen exhibits much higher toughness than that of the crosslinked PIB-PU (3,018 g/mole) (Table 5).

TABLE 5

Young's modulus, tensile strength, and elongation at break of crosslinked PIB—PUs prepared with Ø(PIB—OH)₃ of 3,018 and 9,000 g/mole.

| Sample (Mn, g/mole) | Young's modulus (MPa) | Stress (MPa) | Strain (%) | Toughness (J) |
|---|---|---|---|---|
| xPIB—PU 3,018 | 29.9 ± 1 | 13.8 ± 0.1 | 199.0 ± 5 | 0.25 |
| xPIB—PU 9,000 | 41.5 ± 0.5 | 13.0 ± 0.5 | 425.0 ± 8 | 1.10 |

In order to demonstrate practice of the invention, one or more examples have been prepared. The following examples are exemplary in nature and the present invention is not limited thereto. Rather, as is noted above, the present invention relates to the production and/or manufacture of various multiply-crosslinked polyurethanes (xPIB-PUs), related articles made therefrom.

Materials and Techniques (IB) was from Scott Specialty Gases B.V. 2,6-di-tert-butylpyridine (DTBP), N,N-dimethylacrylamide (DMAA) and titanium (IV) chloride (TiCl$_4$) from Sigma-Aldrich were used without purification. Allyltrimethylsilane (ATMS), methylene chloride (CH2Cl2) (Sigma-Aldrich) and n-hexane (Merck) were distilled over. CaH$_2$ is under reduced pressure and kept under a N$_2$ atmosphere. Tetrahydrofuran (THF, Sigma-Aldrich) was distilled from sodium benzophenone before use. 4,4'-Methylenebis (phenyl isocyanate) (MDI, Sigma-Aldrich) was distilled under reduced pressure and stored at −20° C. under a N$_2$ atmosphere. 1,4-Butanediol (BDO, Sigma-Aldrich) was distilled under reduced pressure over a small piece of sodium metal and stored under a N$_2$ atmosphere.

The preparation of 5-tertbutyl-1,3-bis(1-chloro-1-methylethyl) benzene (tBuDiCumCl) was described. It was recrystallized from hexane under a N$_2$ atmosphere before use.

Syntheses of Tert-Butyl-Dicumyl Chloride (tBudi-CumCl) and HO-PIB-OH

The syntheses and characterizations of both tBudi-CumCl and HO-PIB-OH have been described in detail. Nowadays, the decent method to synthesize HO-PIB-OH is the polymerization of isobutylene by tBudi-CumCl as bifunctional initiator in conjunction with TiCl$_4$, and termination with allyltrimethylsilane that yields allyl-telechelic polyisobutylene-based (A-PIB-A), which is converted by hydroboration/oxidation to target HO-PIB-OH.

Syntheses of Tri-Functional Initiator

Trimesic acid (TMA, Aldrich) (25 g, 0.12 mole), was esterified to trimethyl-1,3,5-benzenetricarboxylate (TMBTC) by refluxing for two days in CH$_3$OH (810 ml, 20 mole) in the presence of concentrated H$_2$SO$_4$ (76 ml). The solution temperature was lowered to 0° C., the precipitate formed was filtered and the filtrate was washed with water until acid-free. The wet solid was dried at 50° C. under reduced pressure and recrystallized from methanol. Finally, a colorless solid was obtained with a yield of 98.3% (29 g). $^1$H NMR spectroscopy using CDCl$_3$ showed resonances at 4.00 and 8.90 ppm characteristic of methyl protons of the ester groups and aromatic protons, respectively. Ester functionality was greater than 99%.

Then, 1,3,5-tris(1-hydroxy-1-methylethyl) benzene (THMEB) was synthesized from TMBTC through Grignard reaction: in a 500 mL round bottom flask equipped with a magnetic stirring bar, pressure equalized dropping funnel under dry N$_2$ atmosphere a solution of TMBTC (10 g, 0.04 mole) in anhydrous THF (120 ml) was cooled to 0° C. Then a solution of MeMgBr in diethyl ether (Aldrich, 300 mL, 1 M) was added dropwise and the system was stirred at 0° C. for 20 hrs. The mixture was poured into a mixture of 240 g crushed ice and 17 g NH$_4$Cl, extracted with ethyl ether, and dried with anhydrous Mg(SO$_4$)$_2$. Afterward, the solution was filtered, and the solvent removed by using rotary evaporator. The crude THMEB was recrystallized from ethyl acetate and dried under reduced pressure. Yield was 9.8 g (>98%). $^1$H NMR spectroscopy using CDCl$_3$ showed resonances at 1.5 and 7.4 ppm characteristic of methyl protons and aromatic protons, respectively. The HO-functionality determined from its 1H NMR spectrum was greater than 99%.

Finally, 1,3,5-tris(1-chloro-1-methylethyl) benzene (TCMEB or tricumyl chloride) was prepared by hydrochlorination of THMEB. HCl was bubbled through a solution of THMEB (5 g, 0.02 mole) in CH$_2$Cl$_2$ (100 mL) under N$_2$ atmosphere at 0° C. for 6 hours. The solvent was removed by rotary evaporator, the product was crystallized from n-hexane and kept at −20° C. It was recrystallized from n-hexane prior to use. $^1$H NMR spectroscopy using CDCl$_3$ showed resonances at 2.00 and 7.75 ppm characteristic of methyl protons and aromatic protons, respectively. $^1$H NMR characterization showed that the Cl$^-$ functionality was greater than 99%.

Synthesis of Trimethyl-1,3,5-Benzenetricarboxylate (TMBTC)

Trimesic acid (TMA, Aldrich) (25 g, 0.12 mole), was esterified by refluxing for two days in CH$_3$OH (810 ml, 20 mole) in the presence of concentrated H$_2$SO$_4$ (76 ml). The solution temperature was lowered to 0° C., the precipitate formed was filtered and the filtrate was washed with water until acid-free. The wet solid was dried at 50° C. under reduced pressure and recrystallized from methanol. Yield was 29 g (>98%). $^1$H NMR spectroscopy using CDCl$_3$ showed resonances at 4.00 and 8.90 ppm characteristic of methyl protons of the ester groups and aromatic protons, respectively. Ester functionality was greater than 99%.

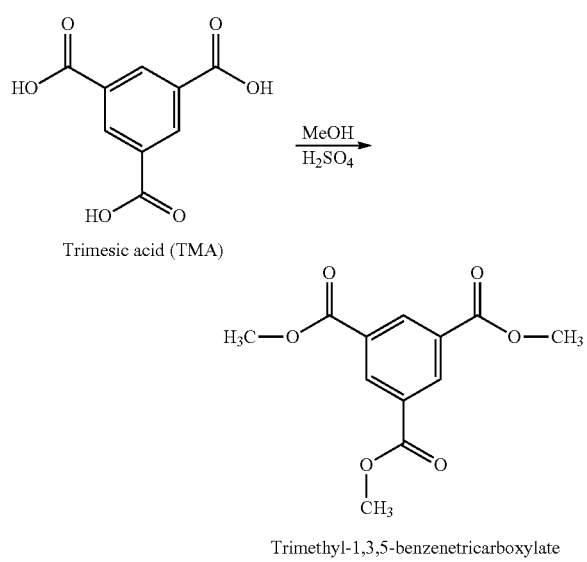

Synthesis of 1,3,5-tris(1-hydroxy-1-methylethyl)benzene (THMEB)

THMEB was synthesized from TMBTC through Grignard reaction: In a 500 ml two neck round bottom flask equipped with a magnetic stirring bar, pressure equalized dropping funnel under dry N$_2$ atmosphere a solution of TMBTC (10 g, 0.04 mole) in anhydrous THF (120 ml) was cooled to 0° C. Then a solution of MeMgBr in diethyl ether (Aldrich, 300 mL, 1 M) was added dropwise and the system was stirred at 0° C. for 20 hours. The mixture was poured into a mixture of 240 g crushed ice and 17 g NH$_4$Cl, extracted with ethyl ether, and dried with anhydrous Mg(S04)2. Afterward, the solution was filtered, and the solvent removed by using rotary evaporator. The crude THMEB was recrystallized from ethyl acetate and dried under reduced pressure. Yield was 9.8 g (>98%). $^1$H NMR spectroscopy using CDCl$_3$ showed resonances at 1.5 and 7.4 ppm characteristic of methyl protons and aromatic protons, respectively. HO-functionality was greater than 99%. HO-functionality was greater than 99%.

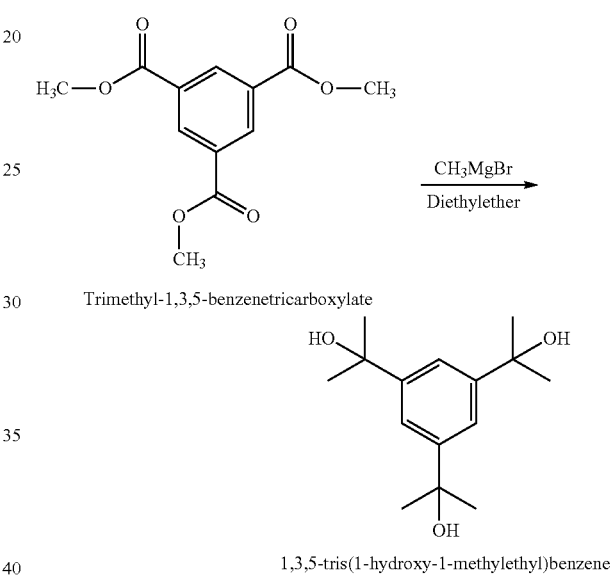

Synthesis of 1,3,5-tris(1-chloro-1-methylethyl)benzene (TCMEB-tricumyl Chloride)

The TCMEB was prepared by hydrochlorination of THMEB. So that HCl was bubbled through a solution of THMEB (5 g, 0.02 mole) in CH$_2$Cl$_2$ (100 mL) under N$_2$ atmosphere at 0° C. for 6 hours. The solvent was removed by using rotary evaporator, the product was crystallized from n-hexane and kept in freezer at −20° C. It was recrystallized from n-hexane prior to use. $^1$H NMR spectroscopy using CDCl$_3$ showed resonances at 2.00 and 7.75 ppm characteristic of methyl protons and aromatic protons, respectively. Cl$^-$ functionality was greater than 99%.

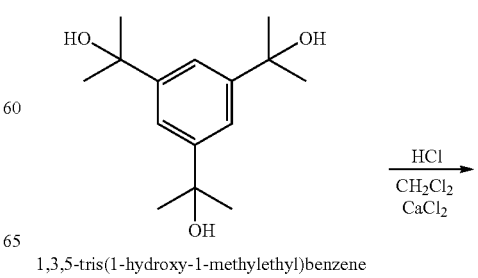

1,3,5-tris(1-hydroxy-1-methylethyl)benzene

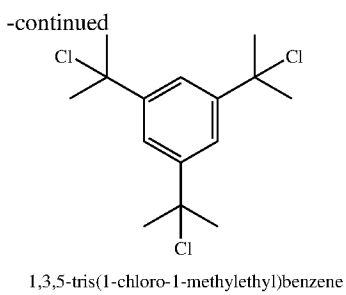

1,3,5-tris(1-chloro-1-methylethyl)benzene

Synthesis of Three-Arm Star Allyl-Telechelic PIB [Ø(PIB-allyl)₃]

To a 1-liter flame-dry round bottom flask equipped with a mechanical stirrer, TCMEB was added (20 g, 65 mmole). Hexane (200 mL), dichloromethane (108 mL), 2,6-di-tert-butylpyridine (DTBP, 3.3 mole, 1.4 mL) and N,N-dimethylacrylamide (DMAA 13.2 mmole, 1.4 mL) were transferred sequentially to the reaction flask under nitrogen protection. The resulting mixture were then cooled down to −75° C. by using a dry ice/isopropyl alcohol cooling bath. TiCl₄ was diluted in CH₂Cl₂ (30 mL) and introduced to the reaction flask in one shot. Polymerization reaction was conducted for 1 hour, then allyltrimethylsilane (49.5 mmole, 7.9 mL) was added and the reaction mixture stirred for 60 minutes at −75° C. To quench the reaction, 10 mL MeOH was added and stirred for 20 minutes. The organic layer was concentrated via a rotary evaporator and then precipitated in MeOH. The crude polymer was dissolved in 200 mL hexane and 100 ml of NaHCO₃ solution (0.1 g NaHCO₃/ml H₂O) was added. The product was extracted three times with hexane and the pH value was adjusted in the range of 7-8. The purified compound was dried over MgSO₄. After filtering MgSO₄ and removing of hexane via rotary evaporator and high vacuum successively at 65° C., the quantitative amount of three-arm star allyl telechelic polyisobutylene-based Ø(PIB-allyl)₃ was obtained. ¹H NMR characterization showed that allyl functionalization was greater than 99% and the predicted molecular weight was attained.

Besides, the GPC chromatogram of Ø(PIB-allyl)₃ showed that it has a unimodal molecular weight distribution and predicted molecular weight.

Synthesis of Three-Arm Star Hydroxyl-Telechelic Polyisobutylene-Based [ø(PIB-OH)₃]

To a 500 mL round bottom flask equipped with a stir bar, the Ø(PIB-allyl)₃ was added (2.17 mmole, 20 g). 100 mL dry THF was transferred to the reaction flask under nitrogen protection. The reaction was immersed in an ice bath and stirred for 30 minutes. 33 ml 9-BBN (16.3 mmole, 0.5 M in THF) was added dropwise to the reaction. The reaction was carried out for 16 hours at room temperature. The solution was cooled to 0° C. and 20 mL KOH solution (48.9 mmole, 0.14 g KOH/ml MeOH) was added dropwise to the reaction followed by addition of 3.4 mL H₂O₂ solution (60 mmole, 50% w/w). The reaction was carried out for 16 hours at room temperature. 100 ml hexane and 17 ml KHCO₃ (17 mmole, 0.1 g KHCO₃/ml H₂O) solution were added to the reaction mixture and stirred for 1 hour. The reaction mixture was extracted three times with hexane and the pH value was adjusted in the range of 5-6. The organic layer was concentrated via a rotary evaporator and then precipitated in MeOH three times in order to get rid of cyclooctane-1,5-diol. The purified compound was dissolved in hexane and dried over MgSO₄. After filtering MgSO₄ and removing of hexane via high vacuum at 85° C., a colorless viscous product was obtained. ¹H NMR characterization showed that —OH functionalization was greater than 99%.

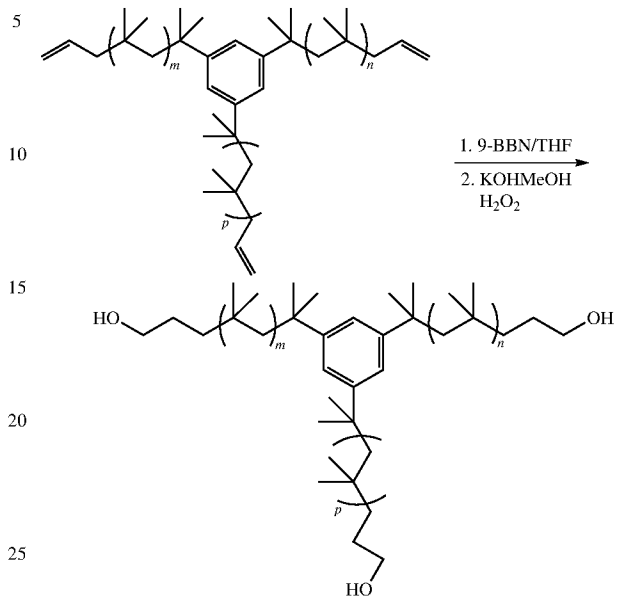

Synthesis of xPIB-PU Crosslinked with Ø(PIB-OH)₃

Synthesis details were essentially the same as those used for the preparation of PIB-PU, except a Ø(PIB-OH)₃ was also used. The soft/hard domain compositions in all xPIB-PUs were 70/30 wt. % to obtain biocompatibility and calcification resistance. The relative amounts of reactants were calculated by the following equations:

$$\frac{W_{\emptyset(PIB\text{-}OH)_3}}{W_{\emptyset(PIB\text{-}OH)_3} + W_{HD}} = 0.7$$

$$W_{HD} = W_{BDO} + W_{MDI}$$

$$n_{\emptyset(PIB\text{-}OH)_3} \times 3/2 + n_{BDO} = n_{MDI}$$

where W=sample weight, n=number of moles, and HD=hard domain.

A representative experiment, using the three-arm star HO-telechelic PIB [Ø(PIB-OH)₃] of 9,000 g/nol MW, fn=−3, was performed as follows: Calculated amounts of Ø(PIB-OH)₃ (0.9 g, 0.10 mmol) and MDI (296.1 mg, 1.183 mmol) were weighed into a 20 mL vial closed by a rubber septum and carrying a small condenser. The vial was degassed under reduced pressure and charged with nitrogen gas. Then, 2.0 mL THF was syringed into the vial under N₂ atmosphere to dissolve the charge. The prepolymer was prepared by adding DBTDL catalyst solution in THF (0.8 mg, 0.0013 mmol-0.4 mL of 2.0 mg/mL), and heating the stirred system in an oil bath at 65° C. Separately, BDO (93.1 mg, 1.033 mmol) was weighed in another flame dried vial closed by a rubber septum. The vial was evacuated at 2.0×10⁻² mmHg, charged with gaseous N₂ and 2.0 mL dry THF was added by a syringe under N₂. Then the BDO solution was transferred to the vial by a steel cannula. Soon the viscosity of the system increased, and 41 minutes after the addition of the BDO chain extender stirring suddenly stopped because of the high viscosity. Thus, the gel time (i.e., the processability period) was 41 minutes for this sample. Subsequently, this orienting experiment was repeated to obtain a sheet of crosslinked polymer for characterization. In this experiment, we poured the still processable highly viscous reaction mixture into a 7×7 cm glass mold after 24 minutes, covered the polymer-filled mold with a flat glass plate leaving a thin opening for slow solvent evaporation. The system was left to cure for 2 days at room temperature, then dried 2 days until weight constancy in a vacuum oven at 60° C. The resulting optically clear film was used for product characterization.

Synthesis of xPIB-PU Crosslinked with a Blend of Ø(PIB-OH)$_3$ and Ø(PIB-OH)$_2$ In these experiments, we prepared xPIB-PUs whose soft domain were homogeneous blends of linear and 3-arm star PIBs. The relative amounts of reactants employed were calculated by the following equations (the abbreviations were introduced in the preceeding section):

$$\frac{n_{\emptyset(PIB-OH)_3} \times 100}{n_{\emptyset(PIB-OH)_3} + n_{\emptyset(PIB-OH)_2}} = \% \ n_{\emptyset(PIB-OH)_3}$$

$$\frac{W_{\emptyset(PIB-OH)_3}}{W_{\emptyset(PIB-OH)_3} + W_{\emptyset(PIB-OH)_2} + W_{HD}} = 0.7$$

$$W_{HD} = W_{BDO} + W_{MDI}$$

$$n_{\emptyset(PIB-OH)_3} \times 3/2 + n_{\emptyset(PIB-OH)_2} + n_{BDO} = n_{MDI}$$

A representative experiment was conducted as follows. In a 50 mL glass vial containing a Teflon-coated ~2 cm stirring bar and sealed with a rubber septum were placed 6 mL THF, and the ingredients for the prepolymer, of PIB-PU containing 70 wt. % PIB [mole % Ø(PIB-OH)$_3$=90: Ø(PIB-OH)$_2$ of Mn=4,000 g/mole, 50.5 mg (1.3×10-2 mmol), Ø(PIB-OH)$_3$ of Mn=3,081 g/mole, 350.0 mg (11.4×10$^{-2}$ mmole) and 138.3 mg (55.3×10$^{-2}$ mmole) MDI]. The temperature was raised to 65° C. to ensure mixing and then 0.2 mL DBTDL solution (8 mg DBTDL/5 mL THF) was added. Prepolymer synthesis was conducted for 1 hour and the solution of 33.3 mg (37.0×10$^{-2}$ mmole) BDO in 1.5 mL THF was transferred to the vial by using a stainless-steel cannula under N$_2$. The charge was stirred at 65° C. and visual observations were made every minutes. Gel time and pouring time were determined.

Synthesis of xPIB-PU by Using Tri-Hydroxy- or Tri-Amino Extender/Crosslinker

The xPIB-PU's were synthesized by using 1,1,1-Tris (hydroxymethyl)ethane (THME) as chemical crosslinking agent and chain extenders. The THME residue settled in the hard domain of the xPIB-PU sample after the reaction was complete.

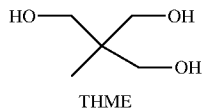

THME

These experiments were developed in two ways. In the first group the amounts of ingredients were controlled to give slow crosslinking (5, 10 and 20 mole % crosslinking agent: TAEA x100/TAEA+BDO, and a xPIB-PU with 70 wt. % soft segment for biocompatibility.

Thus, in a 50 mL glass vial containing a Teflon-coated ~2 cm. stirring bar and sealed with a rubber septum were placed 6 mL THF, and the ingredients for the prepolymerization of PIB-PU containing Ø(PIB-OH)2 of Mn=2900 g/mole (0.90 g, 3.1×10$^{-4}$ mole) and 306.1 mg (1.22×10–3 mole) MDI. The temperature was increased to 65° C. to ensure mixing thoroughly and then 0.5 mL DBTDL solution (8 mg DBTDL/5 mL THF) solution was added. Prepolymerization was conducted for 1 hr. and the mixture of 59.9 mg (6.64× 10-4 mole) BDO and 20.0 mg (1.66×10-4 mole) THME (20 mole % crosslinking agent: THME×100/THME+BDO) in 2 mL of THF was transferred to the vial by using a stainless-steel cannula under N2 atmosphere. The solution was kept at 65° C. and stirred until gelation occurred, as indicated by the stir bar coming to a complete stop. Then, experiments were repeated using 5% and 10% THME (THME×100/THME+ BDO). After determining the gelation time, the experiment was repeated. However, in this case, the content of the vial was immediately poured into a 7×7×0.3 cm glass mold before the gelation process began. The mold was then covered with a glass plate, leaving a small opening to allow the escape of THF. The product was left in the mold under these conditions for three days. Next, the system was heated at 65° C. for three days under reduced pressure in a vacuum oven. Finally, the material recovered from the mold exhibited transparent homogeneous films with satisfactory rubbery properties.

Figure 9:
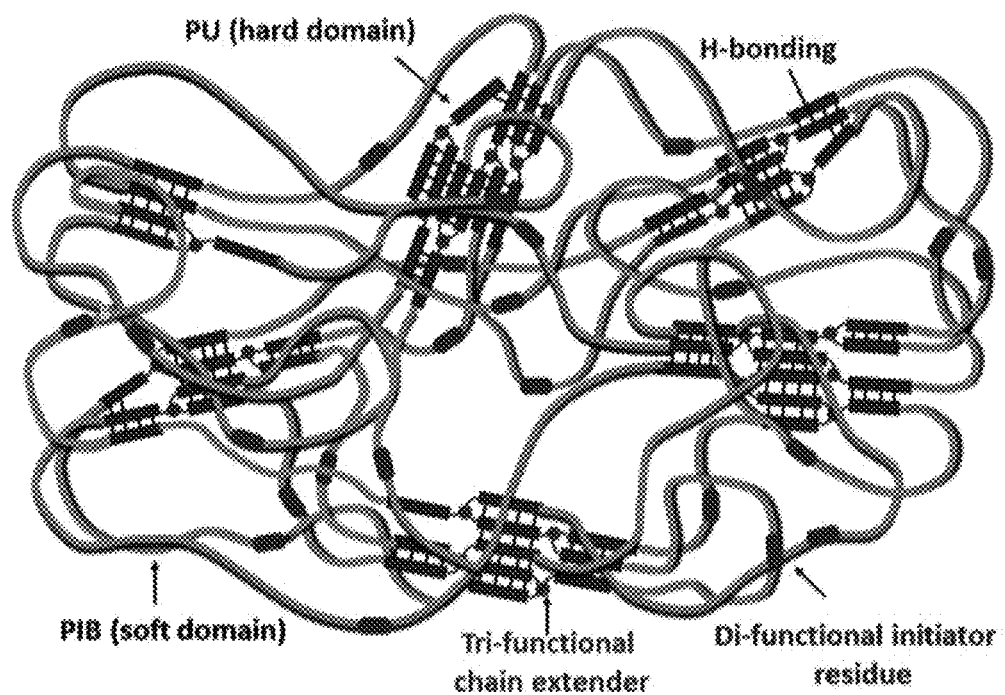
FIG. 9 is an expected microarchitecture of xPIB-PU having a tri-functional chain extender fragments linking hard domains and also showing soft domains.

FIG. 9 shows the idealized microstructure of xPIB-PU having tri-functional chain extender (THME) fragments, hard and soft domains. The little thin lines within the hard phase are meant to indicate H bonds physical crosslinking and reinforcing.

Table 6 summarizes some mechanical properties of the xPIB-PU having a tri-functional chain extender. Specifically, Young's modulus, tensile strength, and elongation at break of xPIB-PUs prepared with Ø(PIB-OH)3 of 3,081 and 9,000 g mole-1, and Ø(PIB-OH)2 of 2,900 g mole-1

TABLE 6

| Sample M$_n$ [g mole$^{-1}$] | Young's Modulus [MPa] | Ultimate Strength [MPa] | Ultimate Strain [%] | Toughness [J] |
|---|---|---|---|---|
| xPIB—PU 3,081 | 29.9 ± 1 | 13.8 ± 0.1 | 199.0 ± 5 | 0.25 |
| xPIB—PU 9,000 | 41.5 ± 0.5 | 13.0 ± 0.5 | 425.0 ± 8 | 1.10 |
| xPIB—PU 2900* | 21.3 ± 1 | 9.4 ± 0.5 | 108 ± 10 | 0.20 |

Table 7 summarizes the creep strain and permanent set of PIB-PU (3,000 g mole$^{-1}$), xPIB-PU (3,081 g mole$^{-1}$), xPIB-PU (9,000 g mole$^{-1}$) and xPIB-PU (2,900 g mole$^{-1}$)

| Sample M$_n$ [g mole$^{-1}$] | Strain [%] | Permanent set [%] |
|---|---|---|
| PIB—PU 3,000 | 13.2 | 1.0 |
| xPIB—PU 3,081 | 11.7 | 1.4 |
| xPIB—PU 9,000 | 5.5 | 1.6 |
| xPIB—PU 2900 | 10.55 | 1.2 |

Creep Resistance

Figure 6:
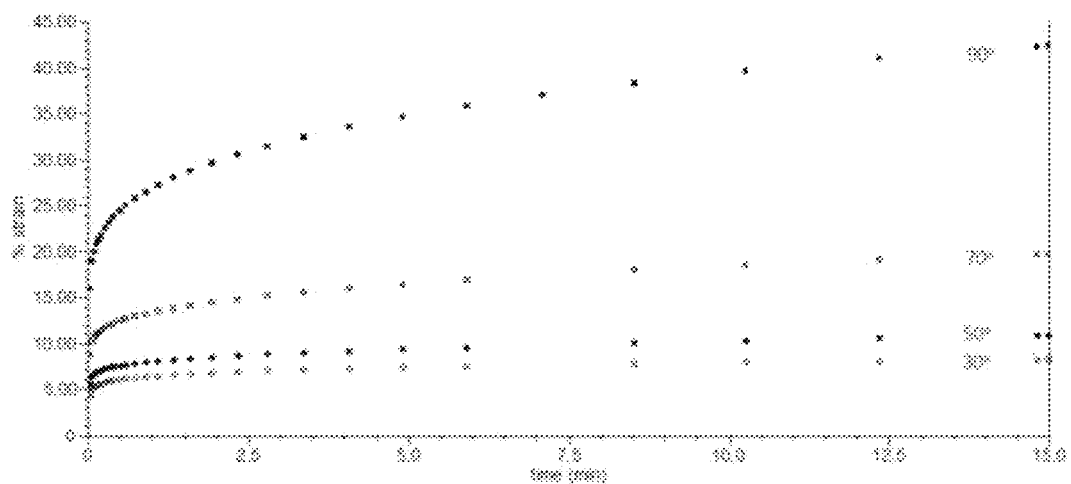
FIG. 6 is a graph showing creep of xPIB-PU(3K) [Mn Ø(PIB-OH)$_3$=3,081 g/mol] at various temperatures.
Figure 7:
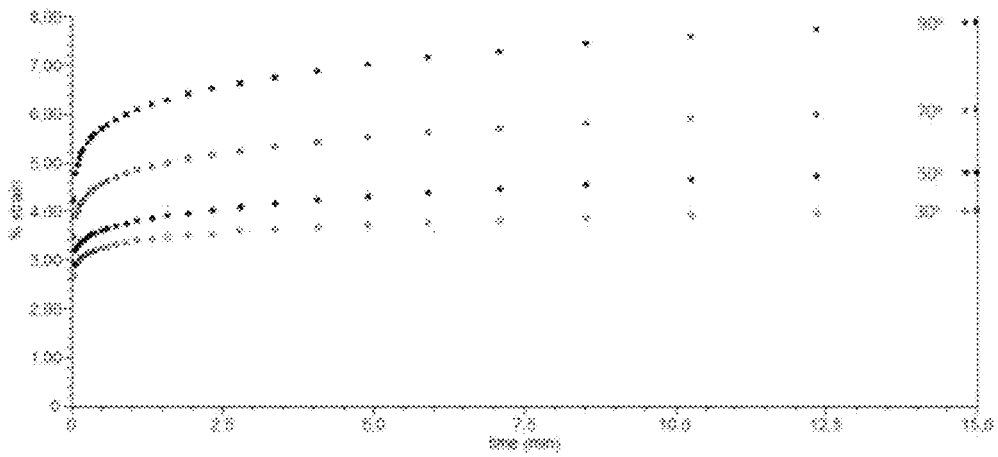
FIG. 7 is graph showing creep of xPIB-PU(9K) [Mn Ø(PIB-OH)$_3$=9,000 g/mol] at various temperatures.

The creep behavior of xPIB-PUs prepared with inicrossers (initiator/crosslinking agent) of Mn=3081 and 9,000 g/mole were studied, the syntheses of these materials, abbreviated xPIB-PU(3k) and xPIB-PU(9k). FIGS. 6 and 7 show creep strain of xPIBPU(3k) and xPIB-PU(9k) versus time at different temperatures, respectively. Relaxation accelerates, creep strain increases, and both compositions deform with increasing temperatures. xPIB-PU(9k) exhibits much higher creep resistance than xPIB-PU(3k). The significant difference in creep strain between these products is most likely due to the higher amounts of crystalline domains in xPIB-PU(9) supported by the chemically crosslinked soft domains.

Creep time-temperature superposition (TTS) experiments provided important further information as to creep behavior. These experiments were carried out using 1.0 MPa stress for 15 mins at 30, 50, 70 and 90° C., and creep deformation was measured in terms of percent strain.

Table 8 summarizes the results of creep strain versus time experiments carried out with double-crosslinked xPIB-PU (3k) and XPIB-PU(9) at 30, 50, 70, and 90° C., and for comparison, with a single-crosslinked PIB-PU synthesized with HO-PIB-OH of Mn=3,000 g/mole soft segment at 30° C. The creep of xPIB-PU (9K) is remarkably low; surprisingly, the creep strain of this product is lower even at 90° C. than that of PIB-PU at 30° C.

TABLE 8

Creep strain of PIB—PU (synthesized with HO—PIB—OH Mn = 3,000 g/mole), xPIB—PU(3) and xPIB—PU(9) at 30, 50, 70 and 90° C.

| Sample (Mn of soft segment, g/mole) | Creep Strain (%) | | | |
|---|---|---|---|---|
| | 30° C. | 50° C. | 70° C. | 90° C. |
| PIB—PU (3,000) | 13.2 | | | |
| xPIB—PU (3,081) | 9.2-11.7 | 12.2 | 20.5 | 43.0 |
| xPIB—PU (9,000) | 4.1-5.5 | 4.9 | 6.1 | 7.8 |

Figure 8:
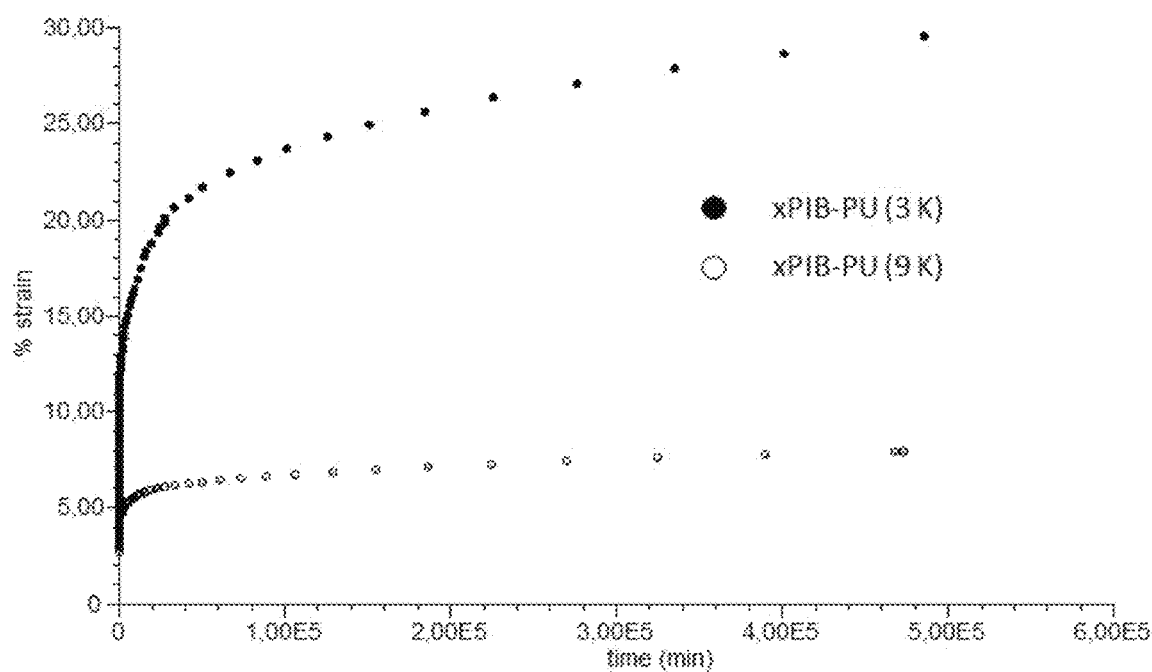
FIG. 8 is a graph showing TTS master curves for xPIB-PU(3K) and xPIB-PU(9K) [Mn Ø(PIB-OH)$_3$=3,081 g/mol and 9,000 g/mol].

FIG. 8 shows the master curve of long-time creep strain generated by Thermal Advantage TTS software of the DMA instrument. xPIB-PU(9K) exhibits high dimensional stability and low creep strain (7.8%) even after 11 months. According to these results xPIB-PU(9K) undergoes minor creep after which it does not creep under the relatively high load of 1 MPa load at 30° C. for many months. At a higher temperature, e.g., at 90° C., creep strain becomes pronounced and keeps increasing very slowly. Evidently, crosslinking the soft phase in PIB-PUs essentially eliminates creep, a very desirable outcome particularly for implantable medical devices.

Thermal Transitions

The study of thermal transitions (Tm, Tg, etc.) provides important insight into the morphology of polymers. The Tg's of the soft PIB phases of xPIB-PU(3K) and xPIB-PU (9K) appear at −52° C. and −64° C., respectively. Since decrease in Mc increases the stiffness of the polymer, such an increase in Tg was expected. The DSC trace of the xPIB-PU(9) clearly shows the presence of a highly crystalline PU domain melting at 202° C. In contrast, the hard PU domain melting range of the linear PIB-PU is in the 180-185° C. range. Evidently, then, the Mn=9000 g/mol inicrosser soft segment increases the stability of the hard PU phase. However, the small broad melting peak that is visible in the xPIB-PU(3) trace at 182° C., and the new Tg that appears at 137° C., suggests that the low Mc in xPIB-PU(3) inhibited PU domain crystallization due to reduced chain mobility, and that some of the PU domains produced amorphous constituents. These observations suggest that the Mc, as determined by the molecular weight of ø(PIB-OH)$_3$, is the critical parameter for the formation and stability of the crystalline domains of xPIB-PU.

In conclusion, Table 5 comprehensively summarizes the properties of PIB-PU and xPIB-PU, comparing them with those of Elast-Eon® E2A, one of the best existing materials for cardiovascular applications belonging to the polysiloxane-based PU family, in cases data for such a comparison was available. PIB-PU and xPIB-PU share comparable physical and mechanical characteristics with polysiloxane-based PUs. Both PIB-PU and Elast-Eon® E2A have tensile strength in the range of 25-35 MPa and an elongation at break exceeding 450%. Both PIB-PU and polysiloxane-based PUs can offer a wide range of Young's moduli and Shore stiffness depending on their chemical structure. The xPIB-PU, on the other hand, has a lower tensile strength and elongation at break but higher stiffness than PIB-PU and Elast-Eon® E2A, due to the addition of covalent crosslinking. In contrast, creep is lower in the case of xPIB-PU given the absence of permanent covalent crosslinking in both PIB-PU and Elast-Eon® E2A.

TABLE 5

Physical, chemical, mechanical, and biological properties of PIB—PU and Elast-Eon E2A.
(PIB content in PIB—PU is 70 wt % unless otherwise stated.)

| Property | xPIB—PU | PIB—PU | Elast-Eon E2A |
|---|---|---|---|
| Physical appearance | Colorless, optically clear | Colorless, optically clear | Colorless, optically clear |
| Density, kg/m$^3$ | | 849-918$^a$ | 1,100 |
| Glass transition temperature, ° C. | | (−73)-(−71)$^a$ (−52)-(−50)$^d$ | (−121)-(−117)$^b$ |
| Melting temperature, ° C. | | 180-200$^c$ | 195-200 |
| Strength (stress at break), MPa | 13.8$^e$ 13.0$^f$ | 32.0$^c$ 26.1$^d$ | 31.0 31.0 20-25 25-35 |
| Elongation at break, % | 199 425 | 630$^c$ 492$^d$ | 450< |
| Young's modulus, MPa | 29.9 41.5 | 16 | 38 35 |
| Hardness, Shore scale | | 77M$^d$ | 89M 90A |
| Creep strain, % | 11.7 5.5 | 13.2 | 9.0 |
| Permanent set, % | 1.4 1.6 | 1.0 | 1.0 |
| Tear energy, kJ/m$^2$ | | | 37-80 |
| Tensile strength retention in PBS after 12 weeks, % | | 90 (55° C.) 57 (85° C.) | 69 (55° C.) 47 (85° C.) |
| Elongation at break retention in PBS after 12 weeks, % | | 92 (55° C.) 57 (85° C.) | 68 (55° C.) 38 (85° C.) |
| Reduction in molecular weight after aging in PBS for 52 weeks at 85° C., % | | 26 | 51 67 |
| Tensile strength retention in 35% HNO$_3$ at R.T. after 4 h, % | | 109 | 3 |
| Elongation at break retention in 35% HNO$_3$ at R.T. after 4 h, % | | 113 | 4 |
| Protein adsorption, μg cm$^2$ | | 1.70-2.00 | 0.89 |
| Calcification, Ca atomic % on surface after 28 days in simulated body fluid | | 0-5 | 13.5 |
| Effective Orifice Area$^g$, cm$^2$ | | 1.1-1.3 | 1.1-1.2 |
| Regurgitation Fraction, % | | 3-5 | 6-10 |
| Durability, million cycles$^{g,h}$ | | 100-225 | 50-250 |

In light of the foregoing, it should be appreciated that the present invention significantly advances the art by providing a heart valve that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A multiply-crosslinked polyisobutylene-based polyurethane comprising a co-network of:
   a plurality of multi-telechelic polyisobutylene-based segments, wherein multi-telechelic polyisobutylene based segments include tri- or higher-telechelic polyisobutylene based segments or blends thereof; and
   a plurality of urethane segments having a plurality of chain extender-based segments therein,
   wherein each end of one of said plurality of urethane segments is linked either to an end of one of said plurality of multi-telechelic polyisobutylene-based segments, or to an end of one of said plurality of chain extender-based segments;
   wherein one or more of said plurality of urethane segments are physically crosslinked to one or more other of said plurality of urethane segments; and
   wherein the plurality of multi-telechelic polyisobutylene-based segments constitute at least 70 weight percent of the polyisobutylene-based polyurethane and the plurality of urethane segments, including the plurality of chain extender-based segments therein, constitute up to 30 weight percent of the polyisobutylene-based polyurethane wherein each segment of the multi-telechelic polyisobutylene polyol-based segments has a number average molecular weight of at least 3,000 g/mol.

2. The multiply-crosslinked polyisobutylene-based polyurethane of claim 1, wherein the plurality of multi-telechelic polyisobutylene-based segments are the polyisobutylene segments resulting from the reactions of a plurality of polyisobutylene polyols with diisocyanate, or the reactions of a blend of a plurality of polyisobutylene polyols and a plurality of polyisobutylene polyamines with diisocyanate.

3. The multiply-crosslinked polyisobutylene-based polyurethane of claim 1, wherein the plurality of multi-telechelic polyisobutylene-based segments are a blend of a plurality of tri-telechelic polyisobutylene triol (Ø(PIB-OH)3)-based segments, and a plurality of linear di-telechelic polyisobutylene diol (Ø(PIB-OH)2)-based segments;
   wherein each end of one of said plurality of urethane segments is linked to one of (a) an end of one of said plurality of tri-telechelic polyisobutylene triol-based segments, (b) an end of one of said plurality of linear di-telechelic polyisobutylene diol-based segments, and (c) an end of one of said plurality of chain extender-based segments; and
   wherein the plurality of tri-telechelic polyisobutylene triol-based segments and linear telechelic polyisobutylene diol-based segments constitute at least 70 weight percent of the polyisobutylene-based polyurethane.

4. The multiply-crosslinked polyisobutylene-based polyurethane of claim 1, wherein said plurality of multi-telechelic polyisobutylene polyol-based segments constitute soft domains of polyisobutylene polymers, while the plurality of urethane segments having a plurality of chain extender-based segments therein constitute hard domains of urethane.

5. The multiply-crosslinked polyisobutylene-based polyurethane of claim 1, wherein the plurality of chain-extender segments are selected from the group consisting of a reaction product of a C2-to C8 polyol, or a reaction product of a mixture of the C2 to C8 polyol and a C2 to C8 polyamine with diisocyanate.

6. The multiply-crosslinked polyisobutylene-based polyurethane of claim 4, wherein the chain extenders are polyols selected from the group consisting of 1,4-butane diol (BDO), and 1,1,1-tris (hydroxymethyl)ethane (THME) and combinations thereof.

7. The multiply-crosslinked polyisobutylene-based polyurethane of claim 4, wherein the chain extenders are polyamines selected from the group consisting of 1,4-diaminobutane (DAB) and tris(2-aminoethyl)amine (TAEA).

8. The multiply-crosslinked polyisobutylene-based polyurethane of claim 1, wherein each multi-telechelic polyisobutylene polyol-based segment has a number average molecular weight of between 3,000 and 10,000 g/mol.

9. A method of preparing the multiply-crosslinked polyisobutylene-based polyurethane of claim 1 comprising the steps of:
   a. providing a multi-telechelic polyisobutylene selected from the group consisting of a hydroxy-terminated, multi-telechelic polyisobutylene and a blend of a hydroxy-terminated, multi-telechelic polyisobutylene and an amine-terminated, multi-telechelic polyisobutylene;
   b. freshly distilling a diisocyanate compound to create a freshly distilled diisocyanate;
   c. reacting the multi-telechelic polyisobutylene with a stoichiometric excess of the freshly distilled diisocyanate to provide a mixture of (i) a polyisobutylene-based prepolymer terminated with isocyanate ends and (ii) diisocyanate; and
   d. adding a stoichiometric amount of a multi-functional cross-linking agent/chain extender to the mixture of the polyisobutylene-based prepolymer and diisocyanate, to charge polymerization of the prepolymer by reacting the cross-linking agent/chain extender with the isocyanate ends of the prepolymer and with the diisocyanate to form urethane groups being chemically cross-linked by covalently bonding the isocyanate ends with the crosslinking agent/chain extender and physical cross-linking the urethane groups by crystalline bonding (H-bonding), thereby forming the multiply-crosslinked polyisobutylene-based polyurethane;
   wherein the multiply-crosslinking polyisobutylene-based polyurethane exhibits a lower percentage of creep as compared to polyisobutylene-based polyurethane that is only physically crosslinked.

10. The method according to claim 9, wherein the step of providing includes providing either a tri-telecheclic polyisobutylene triol, or a blend of a tritelechelic polyisobutylene triol and a di-telechelic polyisobutylene diol.

11. The method according to claim 9, wherein the step of reacting includes reacting a tri-telechelic polyisobutylene triol with a stoichiometric excess of the freshly distilled diisocyanate in the presence of a catalyst to provide a mixture of a polyisobutylene-based three-arm star prepolymer with three urethane-terminated ends and diisocyanate.

12. The method according to claim 9, wherein the step of reacting includes reacting a blend of a tri-telechelic polyisobutylene triol and a di-telechelic polyisobutylene diol with a stoichiometric excess of the freshly distilled diisocyanate in the presence of a catalyst to provide a mixture of a tri-telechelic polyisobutylene-based three-arm star prepolymer with three isocyanate-terminated ends, a di-telechelic polyisobutylene prepolymer with two isocyanate-terminated ends, and diisocyanate.

13. The method according to claim 9, wherein the step of reacting includes covalently bonding a terminal end of the diisocyanate to a terminal end of the multi-telechelic polyisobutylene polyol.

14. The method of claim 9, wherein the step of reacting includes reacting the multi-telechelic polyisobutylene with a stoichiometric excess of the freshly distilled diisocyanate in the presence of a catalyst.

15. The method of claim 9, wherein the step of reacting includes reacting the multi-telechelic polyisobutylene with a stoichiometric excess of the freshly distilled diisocyanate in a solvent.

16. The method according to claim 9, wherein the step of adding includes covalently bonding a terminal end of the diisocyanate to a terminal end of the crosslinking agent/chain extender, to provide multiple diisocyanates linked together by the crosslinking agent/chain extender; and including physically crosslinking multiple diisocyanates together by H-bonding.

17. The method according to claim 9, wherein the cross-linking agent/chain extender is a di-telechelic chain extender, and wherein the step of adding includes adding a stoichiometric amount of the di-functional chain extender to the mixture of the polyisobutylene-based prepolymer and diisocyanate by reacting each end of the di-functional chain extender with either the isocyanate ends of the prepolymer or with the diisocyanate to provide a plurality of urethane groups chemically crosslinked to the polyisobutylene-based polymer, while also enabling the urethane groups to physically bond to each other via H bonding, thereby forming the multiply-crosslinked polyisobutylene-based polyurethane that is crosslinked twice.

18. The method according to claim 9, wherein the cross-linking agent/chain extender is a tri-functional crosslinking agent, and wherein the step of adding includes adding a stoichiometric amount of the tri-functional cross-linking agent, to the mixture of the polyisobutylene-based prepolymer and diisocyanate by reacting each end of the tri-functional cross-linking agent with either the isocyanate ends of the prepolymer or with the diisocyanate to provide a plurality of urethane groups chemically crosslinked to the polyisobutylene-based polymer, while also enabling the urethane groups to physically bond to each other via H bonding, thereby forming the multiply-crosslinked polyisobutylene-based polyurethane that is crosslinked three times.

19. A method for the production of an indwelling device, the method comprising:
   molding the multiply-crosslinked polyisobutylene-based polyurethane of claim 1 into a form suitable for use as the indwelling device.

20. The method of claim 19, wherein the step of molding includes reaction injection molding the multiply-crosslinked polyisobutylene-based polyurethane.

21. The method of claim 19, wherein the indwelling device is selected from the group consisting of heart valves, breast implants, synthetic ligaments, and anti-adhesion shields.

22. An indwelling device comprising the multiply-crosslinked polyisobutylene-based polyurethane of claim 1.

23. A heart valve comprising the multiply-crosslinked polyisobutylene-based polyurethane of claim 1.

* * * * *